US011859209B2

(12) United States Patent
Toguchida et al.

(10) Patent No.: US 11,859,209 B2
(45) Date of Patent: Jan. 2, 2024

(54) METHOD FOR INDUCING OSTEOGENIC DIFFERENTIATION

(71) Applicant: KYOTO UNIVERSITY, Kyoto (JP)

(72) Inventors: Junya Toguchida, Kyoto (JP); Shunsuke Kawai, Kyoto (JP); Hiroyuki Yoshitomi, Kyoto (JP); Cantas Alev, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 587 days.

(21) Appl. No.: 16/954,841

(22) PCT Filed: Dec. 18, 2018

(86) PCT No.: PCT/JP2018/046513
§ 371 (c)(1),
(2) Date: Jun. 17, 2020

(87) PCT Pub. No.: WO2019/124348
PCT Pub. Date: Jun. 27, 2019

(65) Prior Publication Data
US 2021/0087531 A1    Mar. 25, 2021

(30) Foreign Application Priority Data

Dec. 19, 2017 (JP) .................................. 2017-243241

(51) Int. Cl.
*C12N 5/077* (2010.01)
*G01N 33/50* (2006.01)

(52) U.S. Cl.
CPC ....... *C12N 5/0654* (2013.01); *G01N 33/5073* (2013.01); *C12N 2501/999* (2013.01); *C12N 2506/45* (2013.01)

(58) Field of Classification Search
None
See application file for complete search history.

(56) References Cited

U.S. PATENT DOCUMENTS

| 2006/0008902 A1 | 1/2006 | Pike et al. |
| 2016/0002599 A1 | 1/2016 | Eto |
| 2016/0137985 A1 | 5/2016 | Osafune et al. |
| 2016/0289642 A1 | 10/2016 | Osafune et al. |

FOREIGN PATENT DOCUMENTS

| EP | 2730649 A1 | 5/2014 |
| JP | 2002051798 A | 2/2002 |
| WO | WO-2005111197 A1 | 11/2005 |
| WO | WO-2005121319 | 12/2005 |
| WO | WO-2010140698 A1 | 12/2010 |
| WO | WO-2014123242 A1 | 8/2014 |
| WO | WO-2015020113 A1 | 2/2015 |
| WO | WO-2017126616 A1 | 7/2017 |

OTHER PUBLICATIONS

International Preliminary Report on Patentability for Application No. PCT/JP2018/046513, dated Jun. 23, 2020. (English Translation).
International Search Report and Written Opinion for Application No. PCT/JP2018/046513, dated Feb. 20, 2019.
Thanaphum Osathanon et al., "Notch signaling partly regulates the osteogenic differentiation of retinoic acid treated murine induced pluripotent stem cells", *Journal of Oral Science*, vol. 59, No. 3, pp. 405-413 (2017).
Yanhong Yu et al., "Optimized osteogenic differentiation protocol from R1 mouse embryonic stem cells in vitro", *Differentiation*, vol. 89, pp. 1-10 (2015).
Hiroshi Egusa et al., "Comparative Analysis of Mouse-Inducted Pluripotent Stem Cells and Mesenchymal Stem Cells During Osteogenic Differentiation In Vitro", *Stem Cells and Development*, vol. 23, No. 18, pp. 2156-2169 (2014).
Ganna Bilousova et al., "Osteoblasts Derived from Induced Pluripotent Stem Cells Form Calcified Structures in Scaffolds Both in Vitro and in Vivo", *Stem Cells*, vol. 29, pp. 206-216 (2011).
Akira Nasu et al., "Genetically Matched Human iPS Cells Reveal that Propensity for Cartilage and Bone Differentiation Differs with Clones, not Cell Type of Origin", *PLOS One*, vol. 8, Issue 1 (2013).

(Continued)

*Primary Examiner* — Teresa E Knight
(74) *Attorney, Agent, or Firm* — MARSHALL, GERSTEIN & BORUN LLP

(57) ABSTRACT

The present invention provides a method for inducing osteogenic differentiation, the method comprising the following steps of: (1) culturing pluripotent stem cells under feeder-free conditions, (2) culturing the cells in a mixed culture medium of an osteogenic induction medium and a pluripotent stem cell medium, the mixed culture medium containing a ROCK inhibitor and a retinoic acid receptor α or β agonist, and (3) culturing the cells in an osteogenic induction medium containing the retinoic acid receptor α or β agonist. The method for inducing osteogenic differentiation according to the present invention is a simple, short-term, highly efficient and highly reproducible one-procedure method for inducing osteogenic differentiation, wherein the method is suitable for bone regeneration therapies, the development of bone metabolic drugs and the development of novel therapies for bone diseases.

9 Claims, 16 Drawing Sheets

(56) References Cited

OTHER PUBLICATIONS

Makoto Fukuta et al., "Derivation of Mesenchymal Stromal Cells from Pluripotent Stem Cells through a Neural Crest Lineage using Small Molecule Compounds with Defined Media", *PLOS One*, vol. 9 (2014).
Kosuke Kanke et al., "Stepwise Differentiation of Pluripotent Stem Cells into Osteoblasts Using Four Small Molecules under Serum-free and Feeder-free Conditions", *Stem Cell Reports*, vol. 2, pp. 751-760 (2014).
Kyle M. Loh et al., "Mapping the Pairwise Choices Leading from Pluripotency to Human Bone, Heart, and Other Mesoderm Cell Types", *Cell*, vol. 166, pp. 451-467 (2016).
Extended European Search Report in corresponding European Application No. 18892944.2, dated Oct. 21, 2021.
Li et al., "Derivation of Murine Induced Pluripotent Stem Cells (iPS) and Assessment of Their Differentiation Toward Osteogenic Lineage", *Journal of Cellular Biochemistry*, vol. 109, No. 4, pp. 643-652 (2010).

Fig. 2

METHOD FOR INDUCING OSTEOGENIC DIFFERENTIATION

TECHNICAL FIELD

The present invention relates to a novel method for inducing pluripotent stem cells to differentiate into osteocytes. The present invention also relates to a method for screening for a therapeutic drug for bone diseases using the method for inducing osteogenic differentiation.

BACKGROUND ART

Previously described techniques for inducing pluripotent stem cells to differentiate into osteoblasts and then osteocytes are roughly classified into two methods. The first method relies on the formation of embryoid bodies, which promote spontaneous differentiation. Embryoid body-derived cells are attached to culture dishes, and cells with migration ability, which is indicative of mesenchymal cells, are harvested and cultured in osteogenic induction medium conventionally used for bone marrow-derived cell culture to induce terminal differentiation (non-patent literature 1). The other one is a multi-step induction method that uses multiple steps to more faithfully recapitulate the developmental process of bone tissues. This method has been used to induce osteoblasts from the neural crest (non-patent literature 2), the mesoderm (non-patent literature 3) or the somites (non-patent literature 4). The former method is relatively simple, but it requires the formation of embryoid bodies and cannot provide constant results. The latter method is suitable for research on pathological conditions during the developmental process. However, the induction efficiency of terminally differentiated cells varies depending on the efficiency in each step, and the method requires multiple compounds including expensive biologics, and is therefore not suitable for research by comparison of a large number of cell types. Further, both methods are insufficient to induce the more terminally differentiated cells, osteocytes.

Techniques for inducing human pluripotent stem cells to differentiate into cells with bone tissue-forming capacity will largely contribute to regenerative therapies for bone tissues, the development of bone metabolic drugs and the development of novel therapies for bone diseases. However, until now, there is no one-procedure osteogenic differentiation method that is performed in a simple, short-term, highly efficient and highly reproducible manner and is suitable for the above applications.

CITATION LIST

Non-Patent Literature

Non-patent literature 1: Nasu A, et al. Genetically matched human iPS cells reveal that propensity for cartilage and bone differentiation differs with clones, not cell type of origin. PLOS ONE. 2013; 8: e53771.

Non-patent literature 2: Fukuta M, et al. Derivation of mesenchymal stromal cells from pluripotent stem cells through a neural crest lineage using small molecule compounds with defined media. PLOS ONE, 2014; 9: e112291.

Non-patent literature 3: Kanke K, et al. Stepwise Differentiation of Pluripotent Stem Cells into Osteoblasts Using Four Small Molecules under Serum-free and Feeder-free Conditions. Stem Cell Reports 2014; 2: 751-60.

Non-patent literature 4: Loh K M, et al. Mapping the Pairwise Choices Leading from Pluripotency to Human Bone, Heart, and Other Mesoderm Cell Types. Cell. 2016; 166: 451-67.

SUMMARY OF INVENTION

Technical Problem

An object of the present invention is to provide a simple, short-term, highly efficient and highly reproducible one-procedure method for inducing osteogenic differentiation, wherein the method is suitable for bone regeneration therapies, the development of bone metabolic drugs and the development of novel therapies for bone diseases. Another object of the present invention is to provide a method for screening for a therapeutic drug for bone diseases using the method for inducing osteogenic differentiation.

Solution To Problem

The present invention was made to solve the above problems and includes the following.

[1] A method for inducing osteogenic differentiation, the method comprising the following steps of:
(1) culturing pluripotent stem cells under feeder-free conditions,
(2) culturing the cells in a mixed culture medium of an osteogenic induction medium and a pluripotent stem cell medium, the mixed culture medium containing a ROCK inhibitor and a retinoic acid receptor α or β agonist, and
(3) culturing the cells in an osteogenic induction medium containing the retinoic acid receptor α or β agonist.

[2] The method for inducing osteogenic differentiation according to the above [1], wherein the total duration of the culturing steps (2) and (3) is 12 days or less.

[3] The method for inducing osteogenic differentiation according to the above [1] or [2], wherein the duration of the culturing step (2) is 2 days.

[4] A method for screening for a therapeutic drug for a bone disease, the method comprising the following steps of:
(I) culturing pluripotent stem cells under feeder-free conditions,
(II) culturing the cells in a mixed culture medium of an osteogenic induction medium and a pluripotent stem cell medium, the mixed culture medium containing a ROCK inhibitor and a retinoic acid receptor α or β agonist,
(III) culturing the cells in an osteogenic induction medium containing the retinoic acid receptor α or β agonist and a test substance,
(IV) measuring at least one selected from the amount of calcified nodule formation, the amount of calcium salt deposition, the production or secretion level of type I collagen, and the expression level of an osteogenic differentiation-related gene, and
(V) comparing a measured value with that of the cells cultured in an osteogenic induction medium free of the test substance to determine whether the test substance is capable of enhancing osteogenic differentiation capacity of the cells.

[5] The screening method according to the above [4], wherein the total duration of the culturing steps (II) and (III) is 12 days or less.

[6] The screening method according to the above [4] or [5], wherein the duration of the culturing step (II) is 2 days.

[7] The screening method according to any one of the above [4] to [6], wherein the pluripotent stem cells are bone disease-model pluripotent stem cells.

[8] The screening method according to the above [7], wherein the bone disease-model pluripotent stem cells are iPS cells prepared from cells of a patient with a bone disease.

[9] The screening method according to any one of the above [4] to [6], wherein the pluripotent stem cells are healthy human-derived pluripotent stem cells free of abnormalities associated with a bone disease.

Advantageous Effects of Invention

The present invention provides a simple, short-term, highly efficient and highly reproducible one-procedure method for inducing osteogenic differentiation, wherein the method is suitable for bone regeneration therapies, the development of bone metabolic drugs and the development of novel therapies for bone diseases. The present invention also provides a method for screening for a therapeutic drug for bone diseases using the method for inducing osteogenic differentiation.

BRIEF DESCRIPTION OF DRAWINGS

FIG. 2 shows the bone matrix-forming capacity of cells induced to differentiate by the one-procedure osteogenic differentiation method of the present invention, as assessed by alizarin red staining over time.

Figure 18:
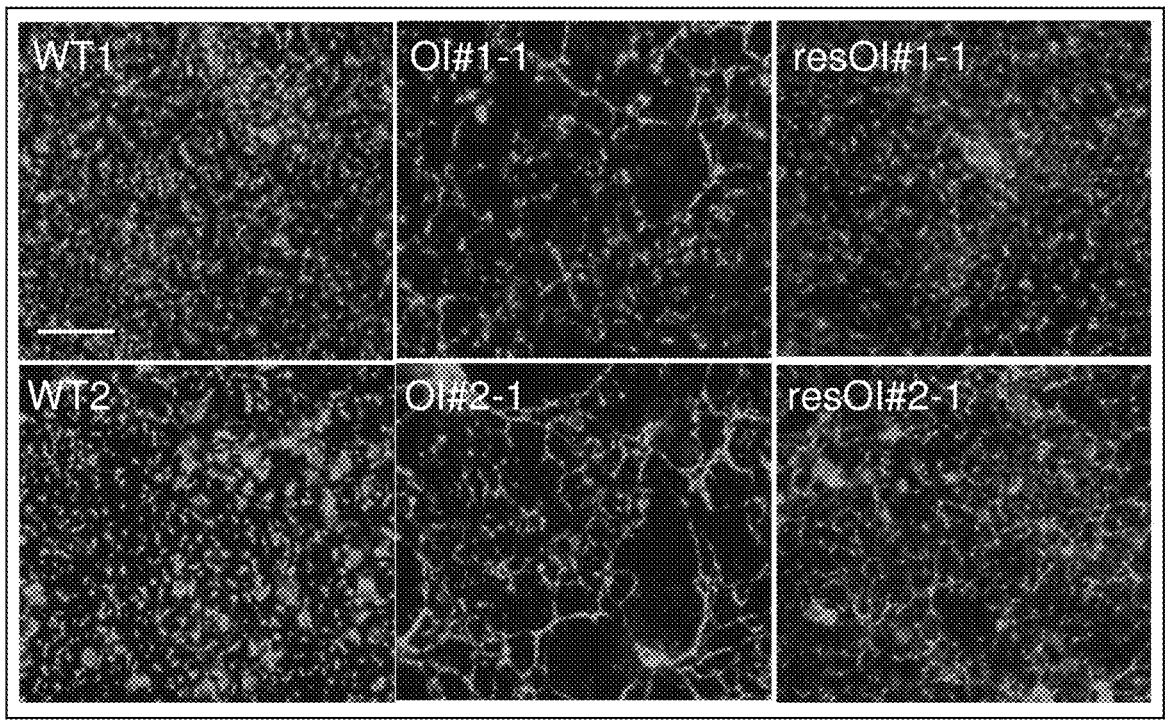

FIG. 18 shows the type I collagen secretion capacity of cells induced to differentiate from iPS cells, as observed by immunostaining with anti-type I collagen antibody. iPS cells were derived from osteogenesis imperfecta patients having abnormalities of the COL1A1 gene. The respective mutations in the COL1A1 gene in the iPS cells were restored by genome editing technology to generate rescued iPS cells. The patient-derived iPS cells, the rescued iPS cells and standard iPS cells were subjected to induction of differentiation by the one-procedure osteogenic differentiation method of the present invention, and the induced cells were immunostained with anti-type I collagen antibody.

Figure 19:
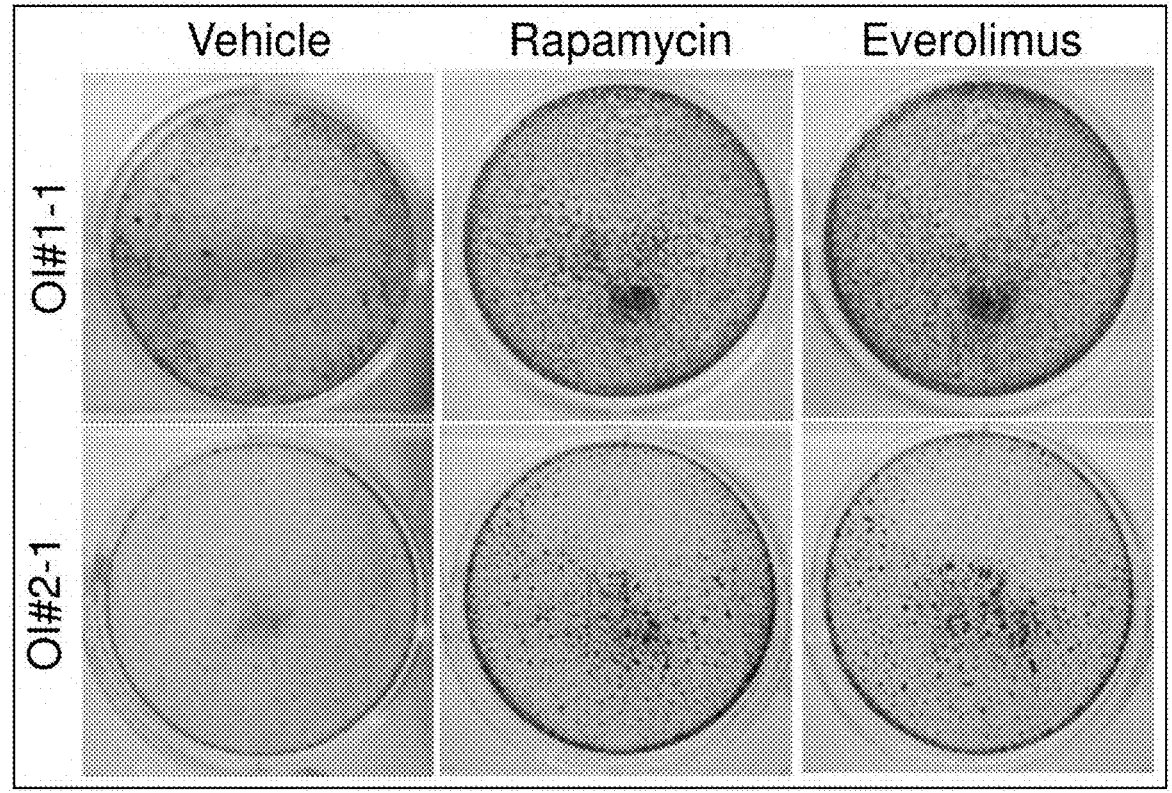

FIG. 19 shows the bone matrix-forming capacity of cells induced to differentiate in culture medium supplemented with rapamycin or everolimus, as assessed by alizarin red staining over time. iPS cells were derived from osteogenesis imperfecta patients having abnormalities of the COL1A1 gene, and were subjected to induction of differentiation in culture medium supplemented with rapamycin or everolimus by the one-procedure osteogenic differentiation method of the present invention, and the induced cells were stained by alizarin red staining over time.

Figure 20:
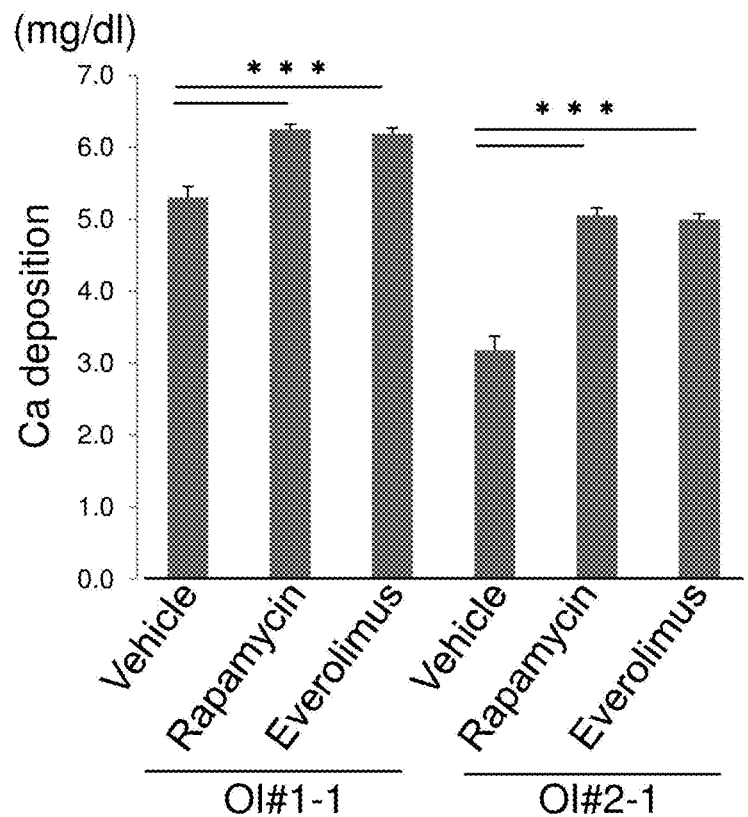

FIG. 20 shows the bone matrix-forming capacity of cells induced to differentiate in culture medium supplemented with rapamycin or everolimus, as assessed by the amount of calcium salt deposition measured over time. iPS cells were derived from osteogenesis imperfecta patients having abnormalities of the COL1A1 gene, and were subjected to induction of differentiation in culture medium supplemented with rapamycin or everolimus by the one-procedure osteogenic differentiation method of the present invention, and the amount of calcium salt deposition was determined over time.

Figure 21:
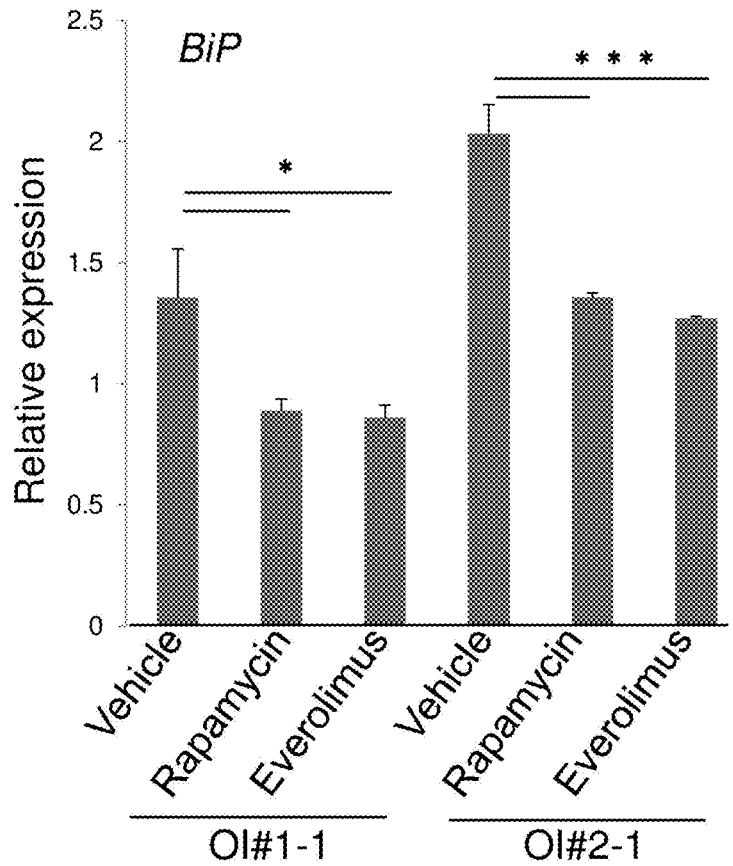

FIG. 21 shows the expression of an endoplasmic reticulum stress-related gene (BiP gene) in cells induced to differentiate in culture medium supplemented with rapamycin or everolimus. iPS cells were derived from osteogenesis imperfecta patients having abnormalities of the COL1A1 gene, and were subjected to induction of differentiation in culture medium supplemented with rapamycin or everolimus by the one-procedure osteogenic differentiation method of the present invention, and the expression of the endoplasmic reticulum stress-related gene BiP in the induced cells was analyzed.

Figure 22:
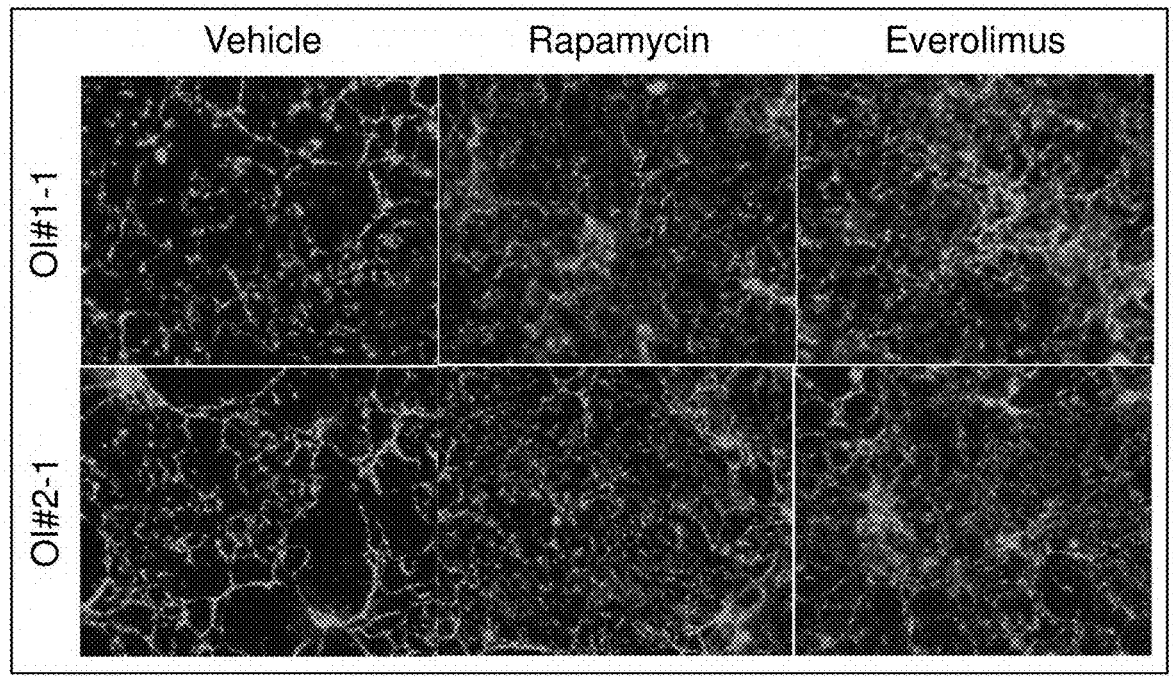

FIG. 22 shows the type I collagen secretion capacity of cells induced to differentiate in culture medium supplemented with rapamycin or everolimus, as observed by immunostaining with anti-type I collagen antibody. iPS cells were derived from osteogenesis imperfecta patients having abnormalities of the COL1A1 gene, and were subjected to induction of differentiation in culture medium supplemented with rapamycin or everolimus by the one-procedure osteogenic differentiation method of the present invention, and the induced cells were immunostained with anti-type I collagen antibody.

Figure 23:
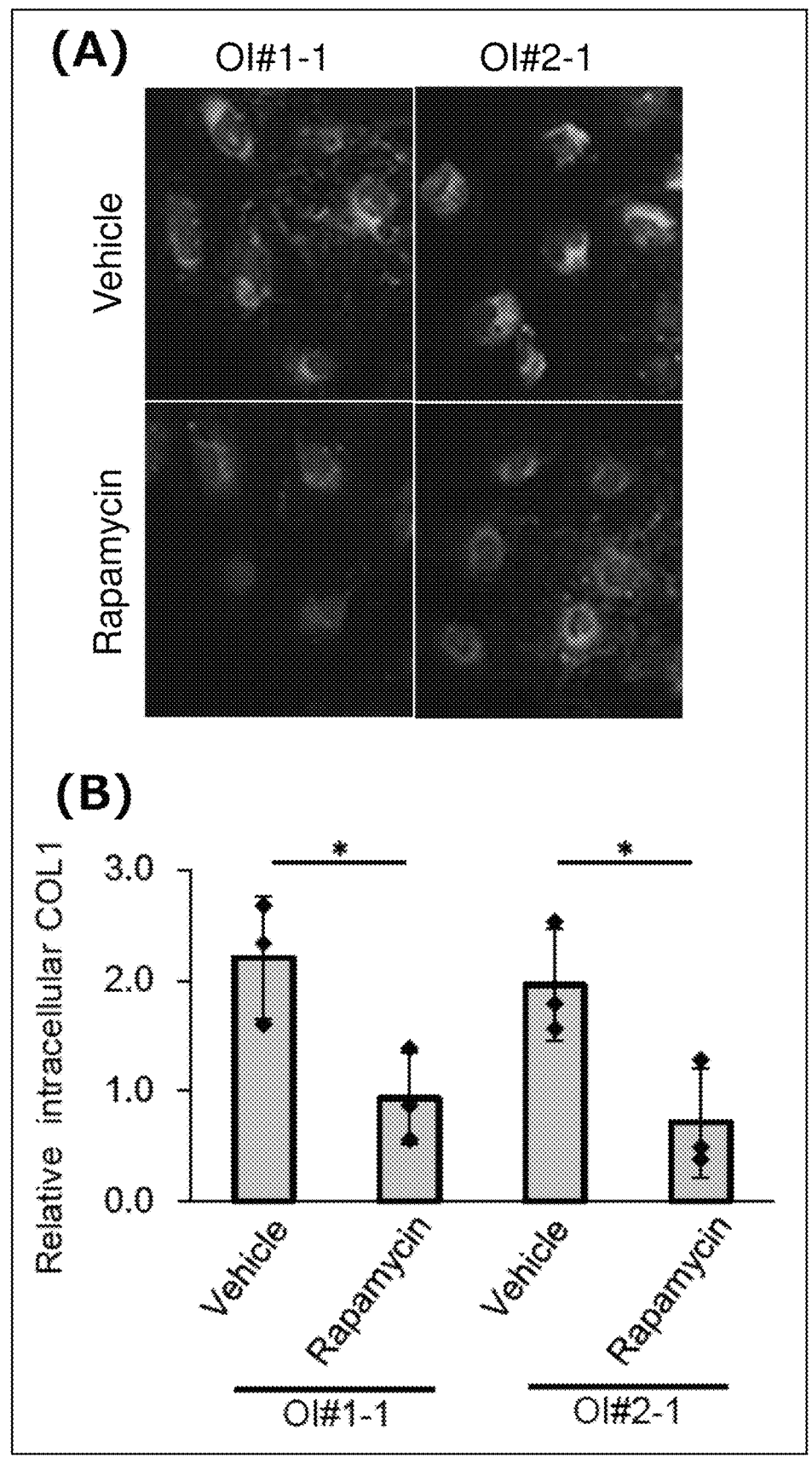

FIGS. 23A and 23B show the amount of accumulated intracellular type I collagen in cells induced to differentiate in culture medium supplemented with rapamycin, as observed by immunostaining with anti-type I collagen antibody and quantified by an image analysis software. iPS cells were derived from osteogenesis imperfecta patients having abnormalities of the COL1A1 gene, and were subjected to induction of differentiation in culture medium supplemented with rapamycin by the one-procedure osteogenic differentiation method of the present invention. The amount of accumulated intracellular type I collagen in the induced cells was observed by immunostaining with anti-type I collagen antibody and quantified by an image analysis software.

DESCRIPTION OF EMBODIMENTS

Method for Inducing Osteogenic Differentiation

The present invention provides a novel one-procedure osteogenic differentiation method for inducing pluripotent stem cells to differentiate into osteocytes. The osteogenic differentiation method of the present invention comprises the following steps:
(1) culturing pluripotent stem cells under feeder-free conditions,
(2) culturing the cells in a mixed culture medium of an osteogenic induction medium and a pluripotent stem cell medium, the mixed culture medium containing a ROCK inhibitor and a retinoic acid receptor α or β agonist, and
(3) culturing the cells in an osteogenic induction medium containing the retinoic acid receptor α or β agonist.

Pluripotent stem cells that can be used in the osteogenic differentiation method of the present invention are any stem cells that have pluripotency, by which the cells are capable of differentiating into all types of cells in the body, and have proliferation potency. Examples of the pluripotent stem cells include embryonic stem (ES) cells, embryonic stem cells from clone embryos obtained by nuclear transplantation (nuclear transfer ES (ntES) cells), spermatogonial stem cells (germline stem (GS) cells), embryonic germ (EG) cells, induced pluripotent stem (iPS) cells, and pluripotent cells (Muse cells) derived from cultured fibroblasts and myeloid stem cells. Preferred are ES cells, ntES cells and iPS cells, and more preferred are iPS cells. The pluripotent stem cells are preferably mammalian pluripotent stem cells. Examples of the mammals include humans, mice, rats, cow and pigs, but are not limited thereto. Preferred are humans. When human pluripotent stem cells are used in the method of the present invention, safe somatic cells that can be used for human regenerative therapies can be obtained. The pluripotent stem cells used in the osteogenic differentiation method of the present invention are free of abnormalities associated with a bone disease, and such pluripotent stem cells are typically those derived from healthy individuals.

In the step (1), the duration of culture of pluripotent stem cells under feeder-free conditions is not limited to a particular period of time. However, when pluripotent stem cells that have been maintained in culture under on-feeder conditions are used in the step (1), the cells are preferably cultured under feeder-free conditions for about 3 days and then subjected to the step (2). More specifically, on-feeder pluripotent stem cells are preferably cultured under feeder-free conditions for at least 66 hours or longer and then subjected to the step (2). When pluripotent stem cells that have been maintained in culture under feeder-free conditions are used in the step (1), the cells are cultured under feeder-free conditions for any given period of time and then subjected to the step (2). The culture of pluripotent stem cells under feeder-free conditions may be performed by any known technique selected as appropriate. For example, the culture can be performed on culture plates coated with an extracellular matrix, such as Matrigel (product name), iMatrix-511 (product name), type IV collagen, fibronectin or vitronectin. The culture medium, culture conditions and other parameters can be selected as appropriate from known culture mediums and conditions suitable for feeder-free culture of pluripotent stem cells. For example, mTeSR medium is preferably used for culture on Matrigel (Ludwig T E, et al. Nat Biotech 2006; 24: 185-187), and StemFit medium is preferably used for culture on iMatrix-511 (Nakagawa M, et al. Sci Rep 2014; 4: 3594).

In the step (2), the cells are cultured in a mixed culture medium of an osteogenic induction medium and a pluripotent stem cell medium, wherein the mixed culture medium contains a ROCK inhibitor and a retinoic acid receptor α or β agonist. A suitable ROCK inhibitor is Y-27632. The amount of Y-27632 added to the mixed culture medium is 9 μM to 11 μM, and is preferably 10 μM. The ROCK inhibitor is Fasudil/HA1077 (Watanabe K, et al. Nature Biotech 2007) or Y-30141 (Ishizaki T, et al. Mol Pharmacol 2000). The amount of Fasudil/HA1077 added to the mixed culture medium is preferably about 10 μM. The amount of Y-30141 added to the mixed culture medium is preferably about 1 μM.

The retinoic acid receptor α or β agonist includes retinoic acid. Examples of the retinoic acid receptor α agonist include Am 580, Am 80 and BMS 753. Examples of the retinoic acid receptor β agonist include CD2314, AC 55649 and AC 261066. The amount of each of retinoic acid receptor α or β agonists added to the culture medium is as follows: the amount of Am 580 is 100 nM to 1 μM, the amount of Am 80 is 500 nM to 5 μM, the amount of CD2314 is 1 μM to 10 μM, and the amount of AC 55649 is 1 μM to 10 μM. The amount of retinoic acid added to the culture medium is 500 nM to 5 μM, and is preferably 1 μM.

The osteogenic induction medium may be any culture medium that can be used for induction of osteogenic differentiation, and includes known osteogenic induction mediums and osteogenic induction mediums that would be developed in the future. A suitable osteogenic induction medium is, for example, Knockout DMEM medium containing 20% FBS, L-glutamine (2 mM), NEAA (1%), β-ME (0.1 mM), β-glycerophosphate (10 mM), dexamethasone (1 nM) and ascorbic acid (50 μg/ml). Other osteogenic induction mediums that can be used include mesenchymal stem cell osteogenic differentiation serum-free medium STK3 (DS Pharma Medical), Mesenchymal Stem Cell Osteogenic Differentiation Medium (PromoCell), Human Mesenchymal Stem Cell Osteogenic Differentiation Medium BulletKit (LONZA), and StemPro Osteogenesis Differentiation Kit (Thermo). The pluripotent stem cell medium may be any culture medium that can be used for culture of pluripotent stem cells, and includes known pluripotent stem cell mediums and pluripotent stem cell mediums that would be developed in the future. Examples of pluripotent stem cell medium that can be used include mTeSR (product name, Stemcell Technologies) and StemFit (product name, Ajinomoto Co., Inc.). The mixing ratio of the osteogenic induction medium and the pluripotent stem cell medium is preferably 3:1 to 5:1, and is more preferably 4:1.

In the step (2), the cells are preferably cultured on gelatin coating or iMatrix-511 (product name) coating. The duration of the culturing step (2) is about 2 days. More specifically, the duration of the culturing step (2) may be 22 hours to 26 hours. In the step (3), on-feeder pluripotent stem cells are preferably cultured on Matrigel or gelatin coating. Feeder-free pluripotent stem cells are preferably cultured on laminin, type IV collagen, fibronectin or vitronectin coating.

In the step (3), the cells are cultured in an osteogenic induction medium containing a retinoic acid receptor α or β agonist. The retinoic acid receptor α or β agonist and the differentiation induction medium are the same as those used in the step (2).

A distinct feature of the osteogenic differentiation method of the present invention is that the total duration of the culturing steps (2) and (3), i.e., the duration of induction of differentiation is as short as 12 days or less. The osteogenic differentiation method can yield terminally differentiated osteocytes usually after 10 days of induction of differentiation. Hence the duration of the culturing step (3) is at least 8 days, and the culturing step (3) does not need to be continued for more than 10 days. The duration of the culturing step (3) may be 8 to 10 days.

The formation of osteocytes by the osteogenic differentiation method of the present invention can be confirmed by assessing the induced cells in terms of the formation of calcified nodules, the deposition of calcium salts, the production or secretion of type I collagen, the expression of osteocyte-specific genes, etc. at the end of the culturing step (3). The assessment can be carried out by known methods selected as appropriate. The formation of calcified nodules can be assessed by, for example, alizarin red staining of the cells. The deposition of calcium salts can be assessed by, for example, the o-cresolphthalein complexon (OCPC) method. The production or secretion of type I collagen can be assessed by, for example, immunostaining of the cells with type I collagen-specific antibody. The expression of osteocyte-specific genes can be assessed by, for example, determining the expression of the PHEX gene and/or the SOST gene by RT-PCR.

Osteoblasts and osteocytes obtained by the osteogenic differentiation method of the present invention, as well as bone-like nodules formed by these cells and the extracellular matrix can be used in the following applications: bone regeneration therapies; screening for drugs that promote the proliferation of osteoblasts or osteocytes; screening for drugs that have an action on the functions of osteoblasts or osteocytes; the development of a culture method for improving the functions of osteoblasts or osteocytes (the composition of culture medium, oxygen concentration, a scaffold material, physical actions such as traction force, three-dimensional culture, etc.); elucidation of the mechanism of differentiation from osteoblasts into osteocytes; analysis of the extracellular matrix, cytokines and exosomes secreted from osteoblasts or osteocytes; analysis of an interaction between osteoclasts and osteoblasts or osteocytes; and other applications.

The osteogenic differentiation method of the present invention is superior to the conventional methods in the following respects:
(1) pluripotent stem cells are osteogenically differentiated within as short as 10 days, whereas the conventional methods require 3 weeks or longer;
(2) the induction efficiency is stable, whereas the conventional multi-step induction methods suffer from the drawback that the overall induction efficiency is affected by the efficiency of each step;
(3) the cost for the induction of differentiation is lower than that of the conventional methods, which require use of multiple expensive growth factors;

(4) the induction method of the present invention is more suitable for screening for drugs as compared with the conventional methods due to the advantages described in the above (1) to (3); and (5) the induction of differentiation into osteocytes has been confirmed, which has not been clearly confirmed in the conventional methods.

Screening Method

The present invention also provides a method for screening for a therapeutic drug for bone diseases using the osteogenic differentiation method. The screening method of the present invention comprises the following steps:

(I) culturing pluripotent stem cells under feeder-free conditions, (II) culturing the cells in a mixed culture medium of an osteogenic induction medium and a pluripotent stem cell medium, the mixed culture medium containing a ROCK inhibitor and a retinoic acid receptor α or β agonist, (III) culturing the cells in an osteogenic induction medium containing the retinoic acid receptor α or β agonist and a test substance, (IV) measuring at least one selected from the amount of calcified nodule formation, the amount of calcium salt deposition, the production or secretion level of type I collagen, and the expression level of an osteogenic differentiation-related gene, and (V) comparing a measured value with that of the cells cultured in an osteogenic induction medium free of the test substance to determine whether the test substance is capable of enhancing osteogenic differentiation capacity of the cells.

The pluripotent stem cells used in the screening method of the present invention are the same as those that can be used in the osteogenic differentiation method. The pluripotent stem cells used in the screening method of the present invention may be bone disease-model pluripotent stem cells or pluripotent stem cells free of abnormalities associated with a bone disease.

The bone disease-model pluripotent stem cells used in the screening method of the present invention may be, for example, pluripotent stem cells whose bone-forming capacity is enhanced or reduced by drug treatment. The drug may be, for example, a steroid, estrogen, an analog thereof, vitamin $D_3$, or the like. In addition to drug-treated pluripotent stem cells, the cells that can be used include pluripotent stem cells in which the functions of a specific related gene have been modified by genome editing technology, and pluripotent stem cells into which a specific miRNA has been introduced.

The bone disease-model pluripotent stem cells may be iPS cells prepared from the cells of a patient with a bone disease. Specific examples of the bone disease include osteogenesis imperfecta, osteopetrosis, pyknodysostosis, osteopoikilosis, melorheostosis, osteopathia striata, dysosteosclerosis, diaphyseal dysplasia, hypertrophic osteoarthropathy, Paget disease, sclerosteosis, trichodentoosseous dysplasia, osteoporosis (idiopathic osteoporosis, steroidal osteoporosis, osteoporosis with vitamin D deficiency), hypophosphatasia, hypophosphatemic rickets, familial expansile osteolysis, fibrous bone dysplasia, fibrodysplasia ossificans progressiva, progressive osseous heteroplasia, cleidocranial dysplasia, ankylosing spondylitis, ossification of the posterior longitudinal ligament, ossification of the ligamentum flavum, diffuse idiopathic skeletal hyperostosis, osteoarthritis, pseudarthrosis, heterotopic ossification, and malignant tumor-associated osteolysis.

The pluripotent stem cells free of abnormalities associated with a bone disease used in the screening method of the present invention may be pluripotent stem cells derived from healthy individuals. Preferred are pluripotent stem cells derived from healthy humans.

The step (I) of the screening method can be performed in the same manner as the step (1) of the osteogenic differentiation method of the present invention. That is, when pluripotent stem cells that have been maintained in culture under on-feeder conditions are used in the step (I), the cells are cultured under feeder-free conditions for about 3 days or at least 66 hours or longer and then subjected to the step (II). When pluripotent stem cells that have been maintained in culture under feeder-free conditions are used in the step (I), the cells are cultured under feeder-free conditions for any given period of time and then subjected to the step (II).

The step (II) of the screening method can be performed in the same manner as the step (2) of the osteogenic differentiation method of the present invention.

The step (III) of the screening method can be performed in the same manner as the step (3) of the osteogenic differentiation method of the present invention except that the osteogenic induction medium contains a test substance in addition to the retinoic acid receptor α or β agonist. In the step (III), cells cultured in an osteogenic induction medium free of the test substance for the same period of time are provided as a control group.

The test substance is not limited to a particular substance, and examples thereof include a nucleic acid, a peptide, a protein, a non-peptidic compound, a synthetic compound, a fermentation product, a cell extract, a cell culture supernatant, a plant extract, a mammalian tissue extract and a plasma. The test substance may be a novel substance or a known substance. The test substance may be in the form of a salt, and the salt may be a salt with a physiologically acceptable acid or base. The concentration of the test substance is selected as appropriate depending on the test substance used.

After the completion of the culturing step (III), at least one selected from the following is measured in the step (IV): the amount of calcified nodule formation, the amount of calcium salt deposition, the production or secretion level of type I collagen, and the expression level of an osteogenic differentiation-related gene. The measurement items can be measured by the known methods exemplified in the osteogenic differentiation method of the present invention.

In the step (V), the measured value(s) are compared with those of the cells cultured in an osteogenic induction medium free of the test substance (control group) to determine whether the test substance is capable of enhancing the osteogenic differentiation capacity of the cells. In other words, when the test substance shows a higher value in the selected measurement item(s) than that of the control group, the test substance can be determined to be capable of enhancing the osteogenic differentiation capacity of the cells. The test substance capable of enhancing the osteogenic differentiation capacity may have a measured value that is 10% higher, 20% higher, 30% higher, 40% higher, or 50% higher than that of the control group.

The test substance that has been determined to be capable of enhancing the osteogenic differentiation capacity by the screening method of the present invention is useful as an active ingredient of a medicament for treatment of various bone diseases. Examples of the bone disease to be treated with such a medicament include, but are not limited to, osteogenesis imperfecta, osteopetrosis, pyknodysostosis, osteopoikilosis, melorheostosis, osteopathia striata, dysosteosclerosis, diaphyseal dysplasia, hypertrophic osteoarthropathy, Paget disease, sclerosteosis, trichodentoosseous dysplasia, osteoporosis (idiopathic osteoporosis, steroidal osteoporosis, osteoporosis with vitamin D deficiency), hypophosphatasia, hypophosphatemic rickets, familial expansile osteolysis, fibrous bone dysplasia, fibrodysplasia ossificans progressiva, progressive osseous heteroplasia, cleidocranial dysplasia, ankylosing spondylitis, ossification of the posterior longitudinal ligament, ossification of the ligamentum flavum, diffuse idiopathic skeletal hyperostosis, osteoarthritis, pseudarthrosis, heterotopic ossification, and malignant tumor-associated osteolysis.

EXAMPLES

The present invention will be described in more detail below with reference to Examples, but the present invention is not limited thereto.

Example 1

Figure 1:
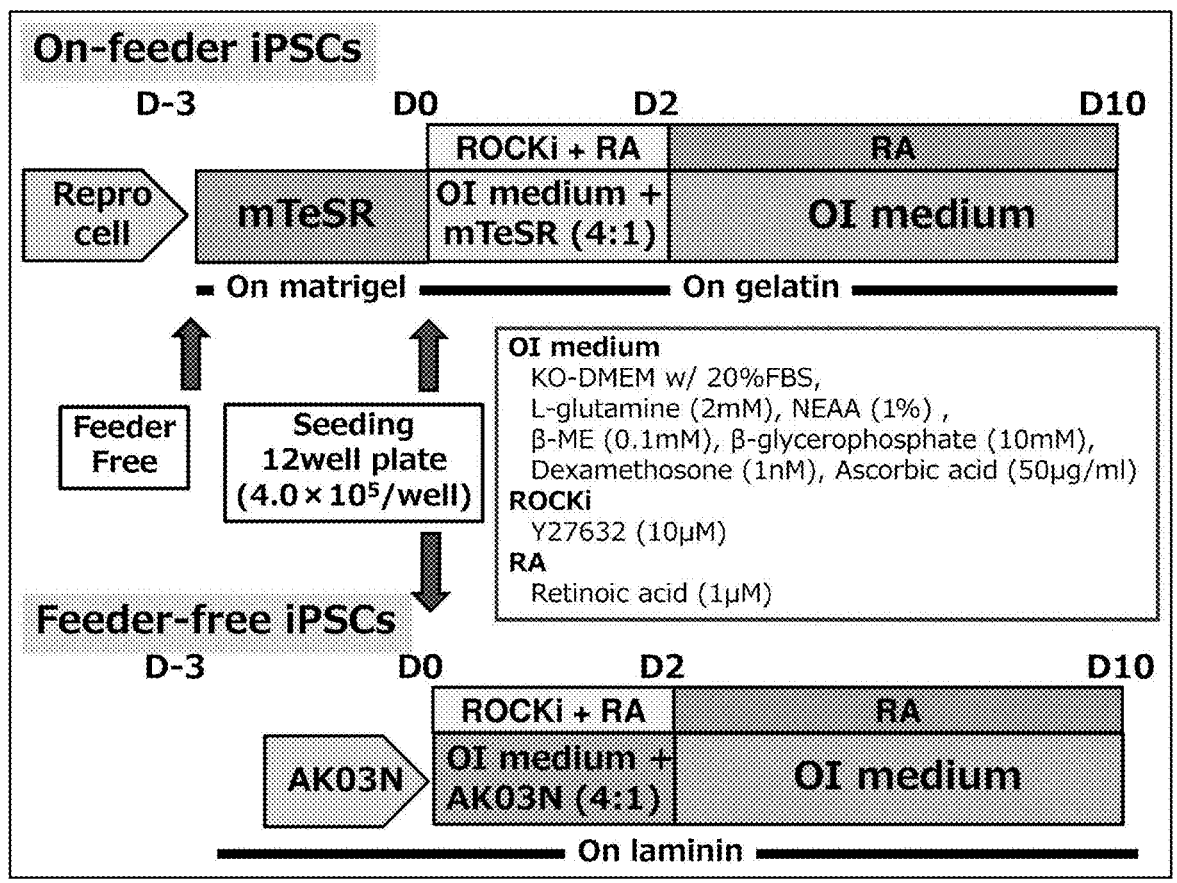
FIG. 1 is a diagram showing the operations of the one-procedure osteogenic differentiation method of the present invention.

Assessment of One-Procedure Osteogenic Differentiation Method Using Retinoic Acid (1) One-Procedure Osteogenic Differentiation Method Using Retinoic Acid (see FIG. 1)

(1-1) Osteogenic Differentiation From On-Feeder iPS Cells (See the Top Row of FIG. 1)

On-feeder iPS cells were cultured under feeder-free conditions on Matrigel coating in mTeSR (product name, Stemcell Technologies) for three days (D-3 to D0). The cells were seeded on gelatin coating and cultured in a mixed culture medium of osteogenic induction medium (OI medium) and mTeSR (mixing ratio=4:1) supplemented with a ROCK inhibitor (ROCKi) and retinoic acid (RA) for the first two days (D0 to D2). The cells were then cultured in osteogenic induction medium supplemented with retinoic acid (RA) until D10. As a control, cells were cultured in the same culture medium without retinoic acid.

(1-2) Osteogenic Differentiation From Feeder-Free iPS Cells (See the Bottom Row of FIG. 1)

iPS cells were cultured under feeder-free conditions on laminin coating in StemFit AK03N (product name, Ajinomoto Healthy Supply), and then cultured in a mixed culture medium of osteogenic induction medium (OI medium) and mTeSR (mixing ratio=4:1) supplemented with a ROCK inhibitor (ROCKi) and retinoic acid (RA) for the first two days (D0 to D2). The cells were then cultured in osteogenic induction medium supplemented with retinoic acid (RA) until D10. As a control, cells were cultured in the same culture medium without retinoic acid.

Figure 2:
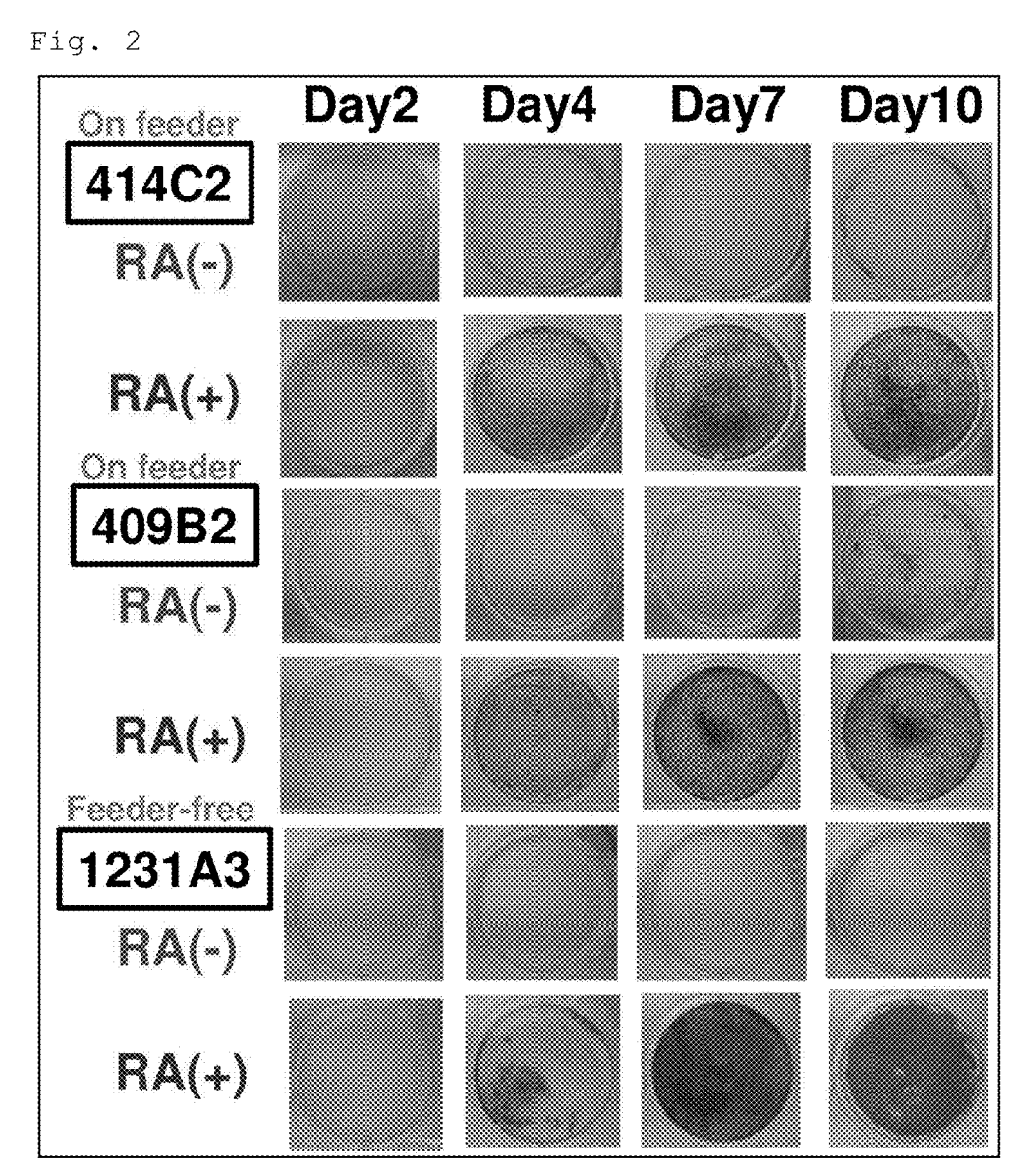
Figure 3:
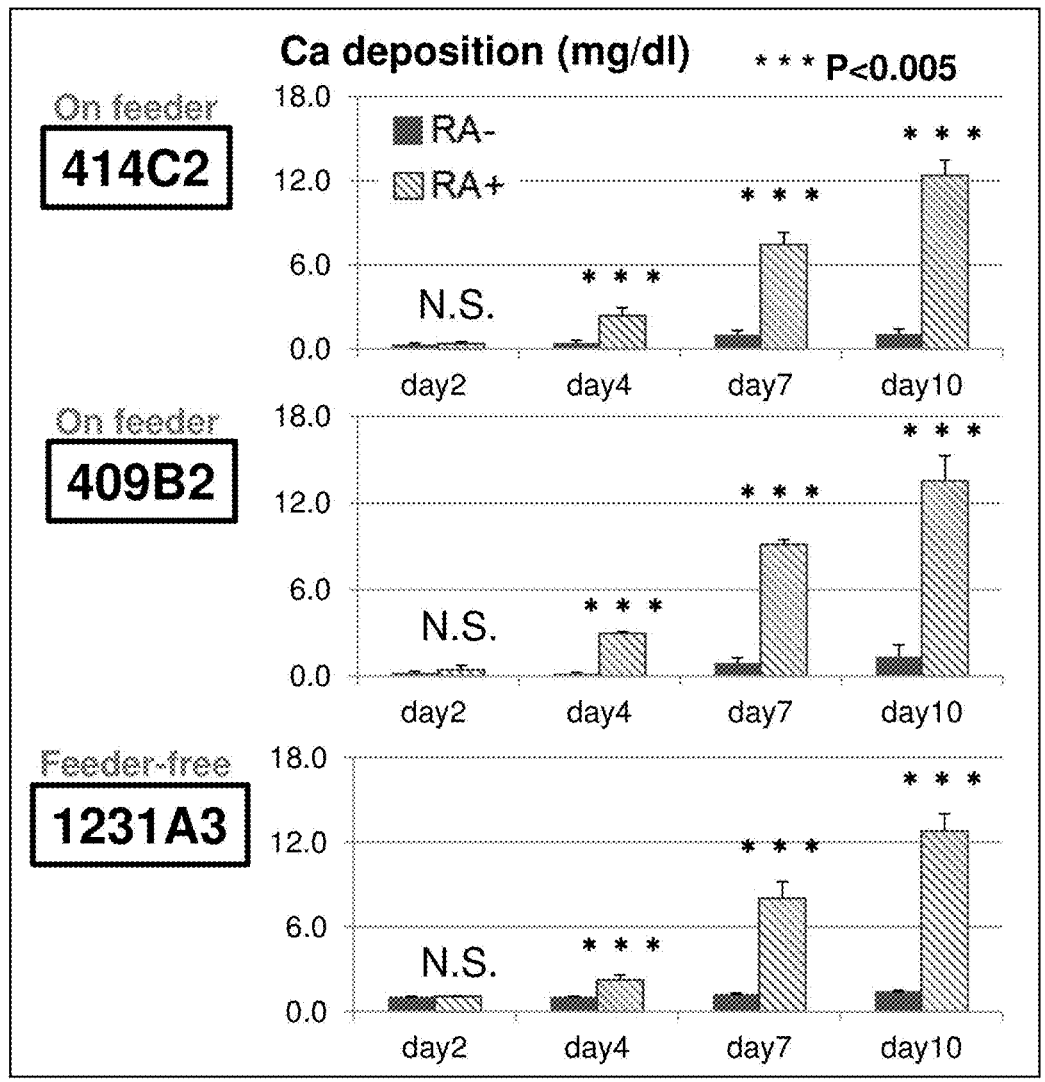
FIG. 3 shows the bone matrix-forming capacity of cells induced to differentiate by the one-procedure osteogenic differentiation method of the present invention, as assessed by determining the amount of calcium salt deposition over time.

(2) Assessment of Osteogenic Differentiation Capacity: Bone Matrix-Forming Capacity For the evaluation of calcified nodule-forming capacity, the cultured cells were fixed in ethyl alcohol, reacted with alizarin red staining solution for 10 minutes and washed. The positive nodules were evaluated qualitatively. Calcium salt deposition was determined quantitatively by measuring the intensity of color produced by o-cresolphthalein complexon (OCPC) solution. FIG. 2 shows the results of alizarin red staining, and FIG. 3 shows the amount of calcium salt deposition. On-feeder cells (414C2 and 409B2) and feeder-free cells (1231A3) cultured with retinoic acid demonstrate significantly enhanced osteogenic differentiation capacity.

(3) Assessment of Osteogenic Differentiation Capacity: Gene Expression

The mRNA expression levels of representative genes expressed at different differentiation stages from pluripotent stem cells to terminally differentiated cells were analyzed over time. Cells were harvested at different periods of time. RNAs were extracted and cDNAs were synthesized. Quantitative PCR was performed using primers specific for each gene to determine the expression levels.

Figure 4:
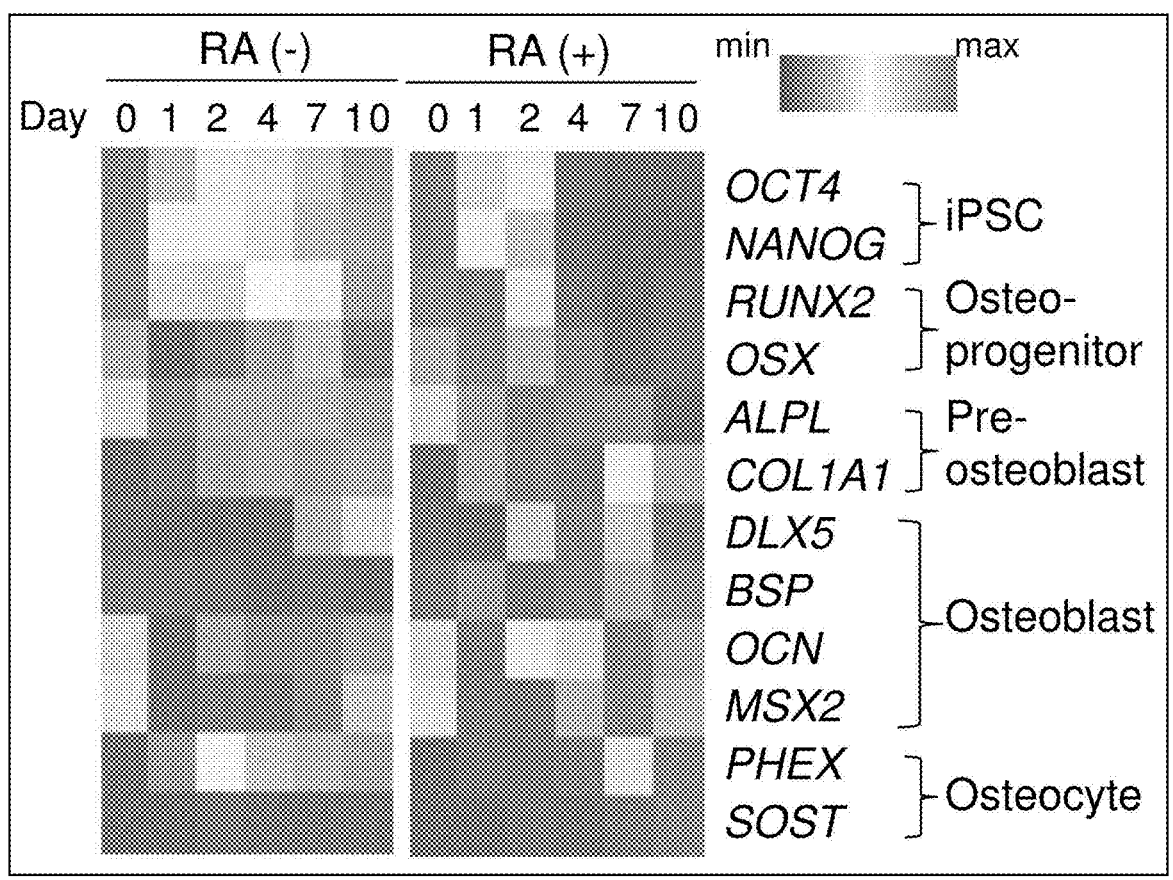
FIG. 4 shows the time-course analysis of expression of representative genes at the mRNA level at different differentiation stages of cells induced to differentiate by the one-procedure osteogenic differentiation method of the present invention.

The results are shown in FIG. 4. The cells cultured without retinoic acid ("RA (−)" in FIG. 4) expressed iPS cell-specific genes on Day 0 and osteoprogenitor-specific genes on Day 10, but the expression of representative genes specific for preosteoblasts and more mature differentiation stages was not observed. On the contrary, the cells cultured with retinoic acid ("RA (+)" in FIG. 4) expressed genes specific for iPS cells, osteoprogenitors, preosteoblasts and osteoblasts over time, and finally expressed the SOST gene specific for osteocytes, which are difficult to obtain from pluripotent stem cells by conventional induction methods. Thus, the results reveal that the one-procedure osteogenic differentiation method using retinoic acid is able to induce human pluripotent stem cells to differentiate into osteocytes within ten days.

(4) Assessment of Osteogenic Differentiation Capacity: Protein Expression

The protein expression levels of representative genes expressed at different differentiation stages from pluripotent stem cells to terminally differentiated cells were analyzed. Cells were fixed in paraformaldehyde and reacted with antibodies against proteins. After washing, the cells were reacted with fluorescent-labeled secondary antibodies, and protein expression was assessed by fluorescence intensity.

Figure 5:
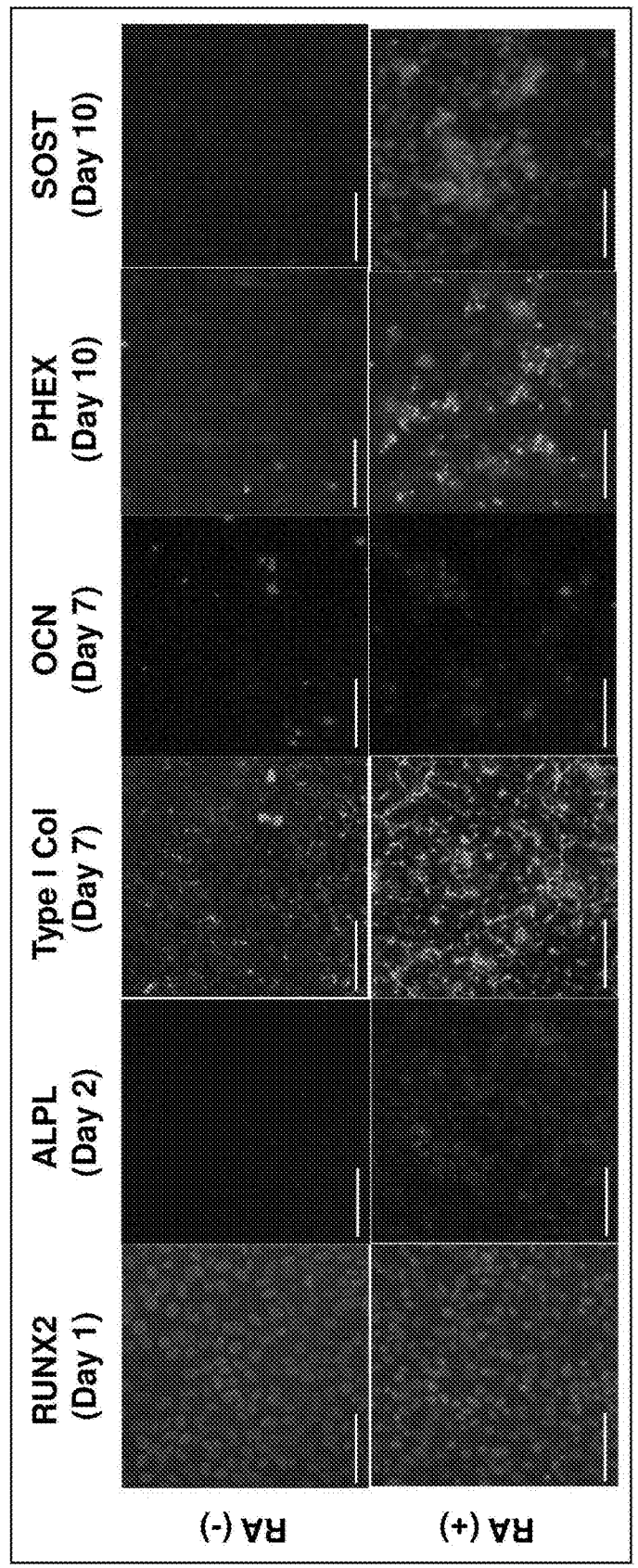
FIG. 5 shows the time-course analysis of expression of representative genes at the protein level at different differentiation stages of cells induced to differentiate by the one-procedure osteogenic differentiation method of the present invention.

The results are shown in FIG. 5. Expression of genes specific for preosteoblasts, osteoblasts and osteocytes was confirmed at the protein level, and these results were consistent with the results of the gene expression at the mRNA level.

(5) Assessment of Osteogenic Differentiation Capacity: Cell Morphology

Figure 6:
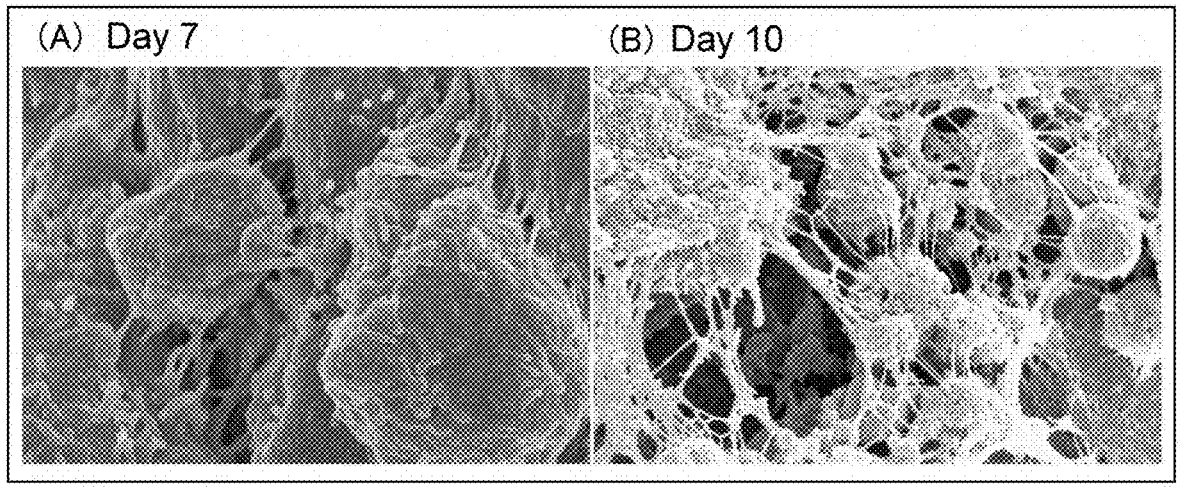
FIGS. 6A and 6B are scanning electron photomicrographs of cells embedded in the matrix harvested on days 7 and 10 of induction of differentiation by the one-procedure osteogenic differentiation method of the present invention.

Cells embedded in the matrix were harvested on days 7 and 10 of induction of osteogenic differentiation and observed with a scanning electron microscope. The results are shown in FIGS. 6A and 6B. FIGS. 6A and 6B show the cells observed on days 7 and 10, respectively. The tissue on day 7 contained relatively spherical cells with a few processes, and the cells on day 10 extended numerous cellular processes to form a network with neighboring cells. These observations were consistent with the morphology of osteoblasts and osteocytes as previously described.

Figure 7:
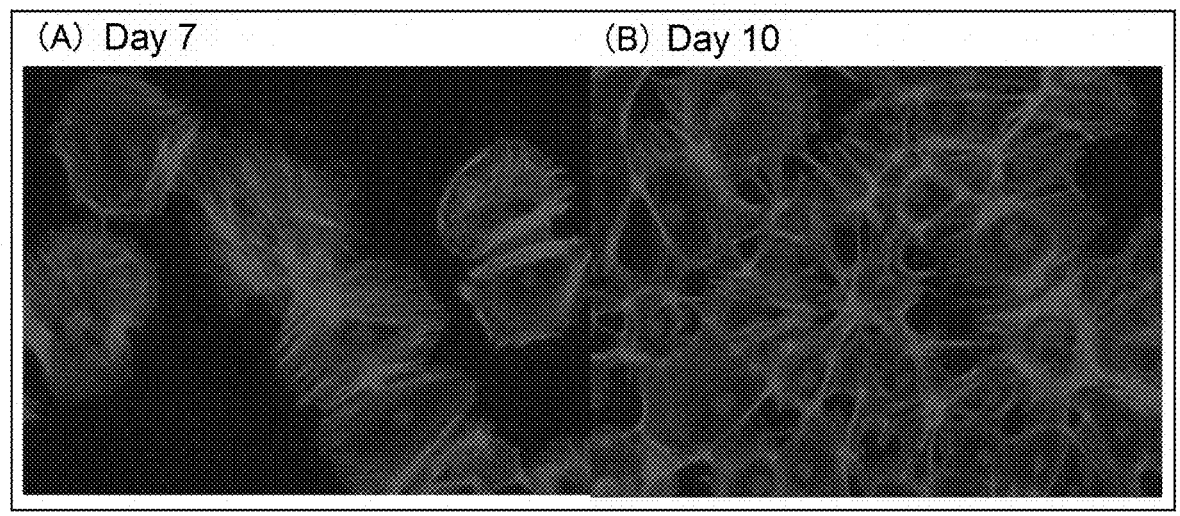
FIGS. 7A and 7B are photomicrographs of single cells that were obtained by dissociating matrix-embedded cells harvested on days 7 and 10 of induction of differentiation by the one-procedure osteogenic differentiation method of the present invention, then reseeded and cultured.

The harvested cells were dissociated as much as possible by collagenase treatment to yield single cells. The single cells were reseed and cultured for several days for morphological observation. The results are shown in FIGS. 7A and 7B. FIG. 7A shows a photomicrograph of cells that were dissociated into single cells on day 7 and reseeded for culture. Many cells with a spherical shape were observed. FIG. 7B shows a photomicrograph of cells that were dissociated into single cells on day 10 and reseeded for culture. Numerous star-shaped cells with a large number of processes as similar to the cells in FIG. 6B were observed. The results indicate that cells with morphology similar to that of osteoblasts and osteocytes in adults were generated by the one-procedure osteogenic differentiation method.

(6) Assessment of Osteogenic Differentiation Capacity: In Vivo Imaging Analysis of Bone-Forming Capacity Cells were harvested as a single mass on day 7, which is the day on which the cells are mainly composed of osteoblasts. The cells were transplanted into bone defects of 4 mm in diameter created in the cranium of NOD-SCID mice. The mice were sacrificed after six weeks, and bone regeneration was examined by micro-CT. Tissue specimens were prepared from the regenerated tissues and stained with HE staining and immunostained with anti-human osteopontin antibody.

Figure 8:
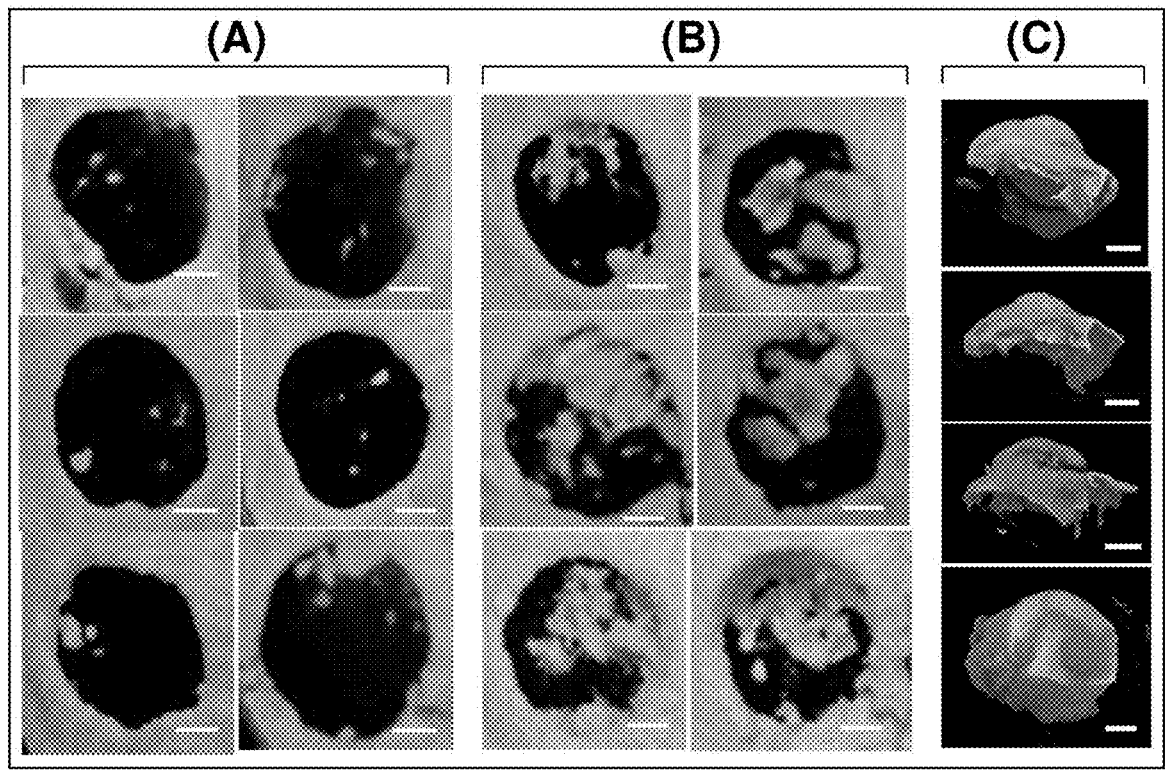
FIGS. 8A to 8C are micro-CT images showing bone regeneration. Cells were induced to differentiate by the one-procedure osteogenic differentiation method of the present invention. On day 7, the cells were transplanted into bone defects of 4 mm in diameter created in the cranium of NOD-SCID mice. After six weeks, the defect sites were photographed by micro-CT.

The images taken by micro-CT are shown in FIGS. 8A to 8C. FIG. 8A shows the micro-CT images of a group with no cell transplantation. FIG. 8B shows the micro-CT images of a group with transplantation of cells cultured in osteogenic induction medium supplemented with retinoic acid. FIG. 8C shows the micro-CT images of a group with transplantation of cells cultured in osteogenic induction medium without retinoic acid. The bone defects were not spontaneously repaired in the group with no cell transplantation as shown in FIG. 8A. Formation of tumors was observed in 4 animals out of 6 in the group shown in FIG. 8C, suggesting the presence of the residual undifferentiated iPS cells. On the contrary, no tumor formation was observed in the group shown in FIG. 8B and bone regeneration was observed. The images in FIGS. 8A and 8B are three-dimensional images reconstructed from CT images of the harvested cranial bones to observe the defects from above. The images in FIG. 8C are three-dimensional visualizations of tumors formed in the defects viewed from the lateral side. The three-dimensional images were reconstructed from CT images of the tumors harvested together with the surrounding cranial bones.

Figure 9:
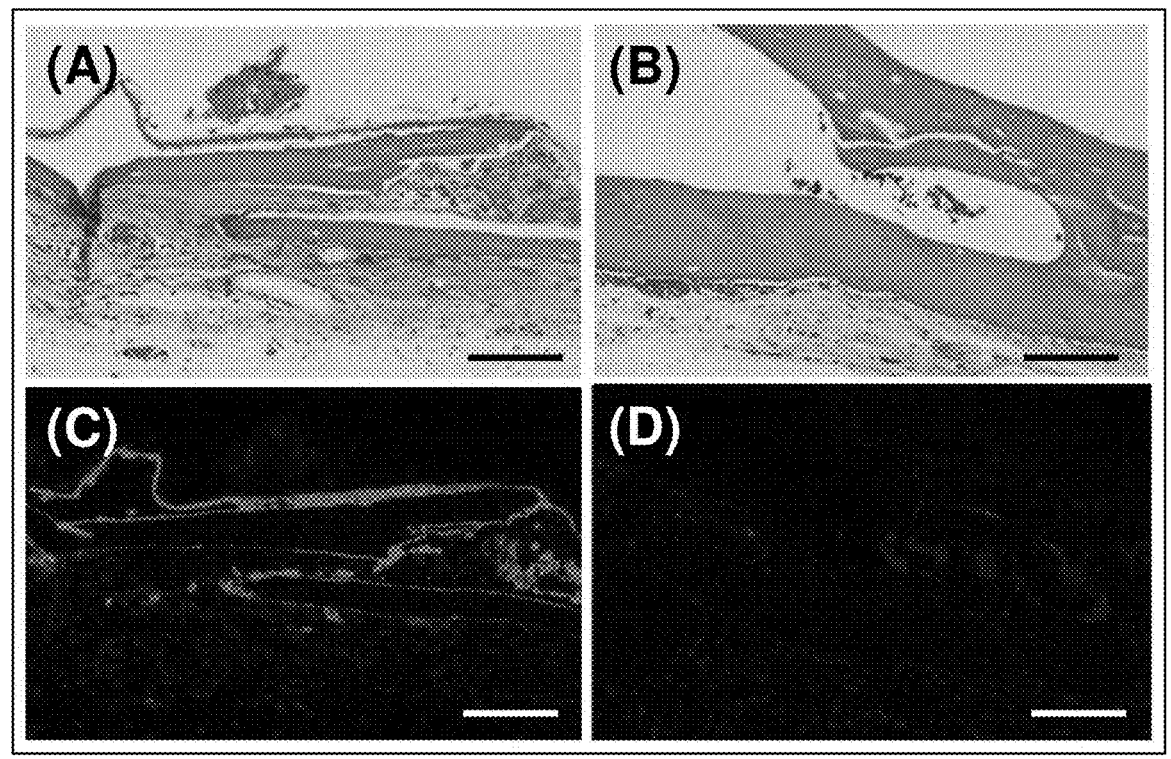
FIGS. 9A to 9D are HE staining images and immunostaining images of regenerated tissues. Cells were induced to differentiate by the one-procedure osteogenic differentiation method of the present invention. On day 7, the cells were transplanted into bone defects of 4 mm in diameter created in the cranium of NOD-SCID mice. After six weeks, the specimens of regenerated tissues were prepared and stained with HE staining or immunostaining with anti-human osteopontin antibody.

FIGS. 9A to 9D show images of regenerated tissues. FIG. 9A is a HE staining image of regenerated tissues in mice transplanted with cells cultured in osteogenic induction medium supplemented with retinoic acid. FIG. 9B is a HE staining image of the cranial bones of untreated NOD-SCID mice. FIG. 9C is an image of anti-human osteopontin antibody immunostaining of regenerated tissues in mice transplanted with cells cultured in osteogenic induction medium supplemented with retinoic acid. FIG. 9D is an image of anti-human osteopontin antibody immunostaining of the cranial bones of untreated NOD-SCID mice. FIG. 9A shows intramembranous ossification similar to that in FIG. 9B. Immunostaining with anti-human osteopontin antibody was performed to confirm the origin of the regenerated tissues. Human osteopontin-positive staining was observed along the newly generated bones in FIG. 9C, whereas the control in FIG. 9D was negative for the staining, indicating that the new bones were derived from the human cells.

Example 2

Investigation of Induction of BMP and WNT Signals by Retinoic Acid

The significance of BMP and WNT signals in the induction of osteogenic differentiation by retinoic acid was investigated.

(1) Induction of Expression of BMP and WNT Signaling Molecules by Retinoic Acid

Figure 10:
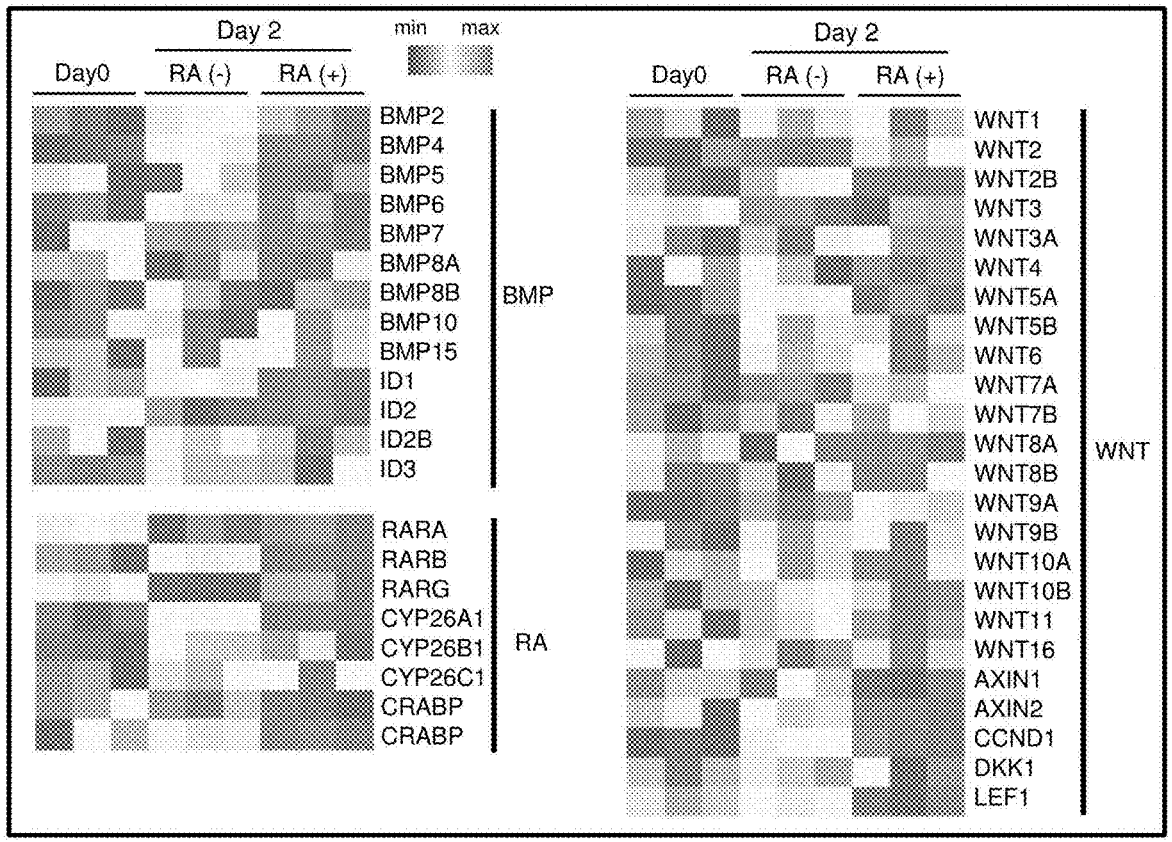
FIG. 10 shows comprehensive gene expression analysis in cells before the start of induction of differentiation (D0) and on day 2 (D2) of induction of differentiation by the one-procedure osteogenic differentiation method of the present invention.

Gene expression before the start of induction of differentiation (D0) and day 2 (D2) of the induction was comprehensively analyzed by microarray. The results are shown in FIG. 10. Relatively high expression of genes during the course of the induction is represented as red in color, and relatively low expression of genes is represented as blue in color. Retinoic acid treatment highly enhanced the expression of molecules downstream of retinoic acid as well as the expression of BMP ligands and their downstream genes and WNT ligands and their downstream genes.

(2) Implications of BMP and WNT in Induction of Osteogenic Differentiation

Figure 11:
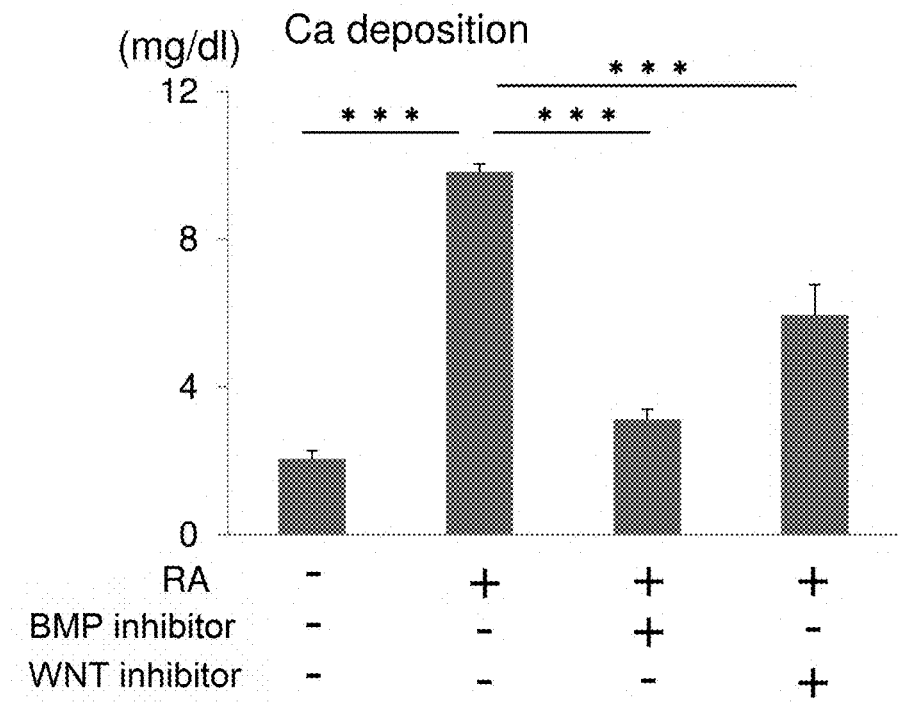
FIG. 11 shows the amount of calcium salt deposition when cells were induced to differentiate in culture medium supplemented with a BMP inhibitor or a WNT inhibitor by the one-procedure osteogenic differentiation method of the present invention, as compared with the amount of calcium salt deposition when cells were induced to differentiate in the absence of the inhibitors.

Next, induction of osteogenic differentiation via BMP and WNT was investigated using inhibitors against them. The results are shown in FIG. 11. Cells were cultured in culture medium supplemented with a BMP inhibitor (LDN) or a WNT inhibitor (IWR1) for 10 days, and the amount of calcium salt deposition was determined. The results indicate that increase in calcium salt deposition by retinoic acid was inhibited. The results confirmed that both of BMP and WNT signals are implicated in the induction of osteogenic differentiation by retinoic acid.

Example 3

Investigation of One-Procedure Osteogenic Differentiation Method Using A Receptor-Specific Agonist Retinoic acid (RA) forms a complex with the nuclear retinoic acid receptor (RAR) α, RARβ or RARγ and binds to a target sequence to exhibit its effects. Based on this mechanism, the inventors investigated whether a receptor agonist can be used as an alternative to retinoic acid in the one-procedure osteogenic differentiation method.

(1) Receptor-Specific Inhibition by an Antagonist or siRNAs

Figure 12:
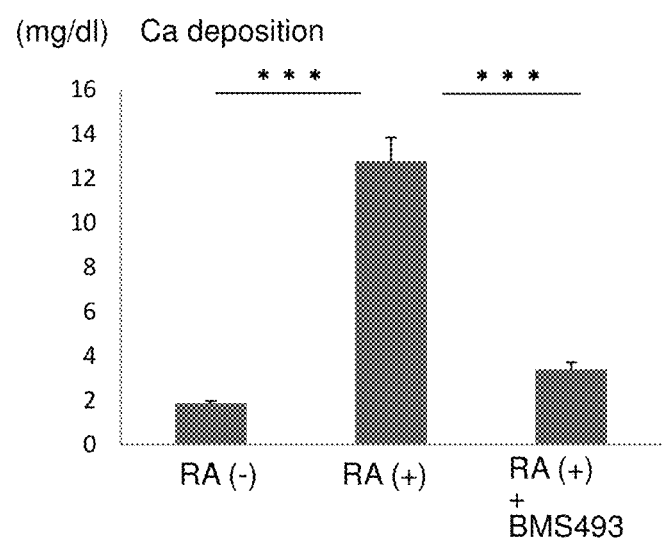
FIG. 12 shows the amount of calcium salt deposition when cells were induced to differentiate in culture medium supplemented with a pan-retinoic acid receptor antagonist (BMS 493) by the one-procedure osteogenic differentiation method of the present invention, as compared with the amount of calcium salt deposition when cells were induced to differentiate in the absence of BMS 493.

Cells were cultured in culture medium supplemented with BMS 493, which is an antagonist against all the retinoic acid receptors (pan-RAR antagonist) for 10 days, and the amount of calcium salt deposition was determined. The effects of RA were completely eliminated, confirming that the effects of RA are mediated by RARs (FIG. 12).

Figure 13:
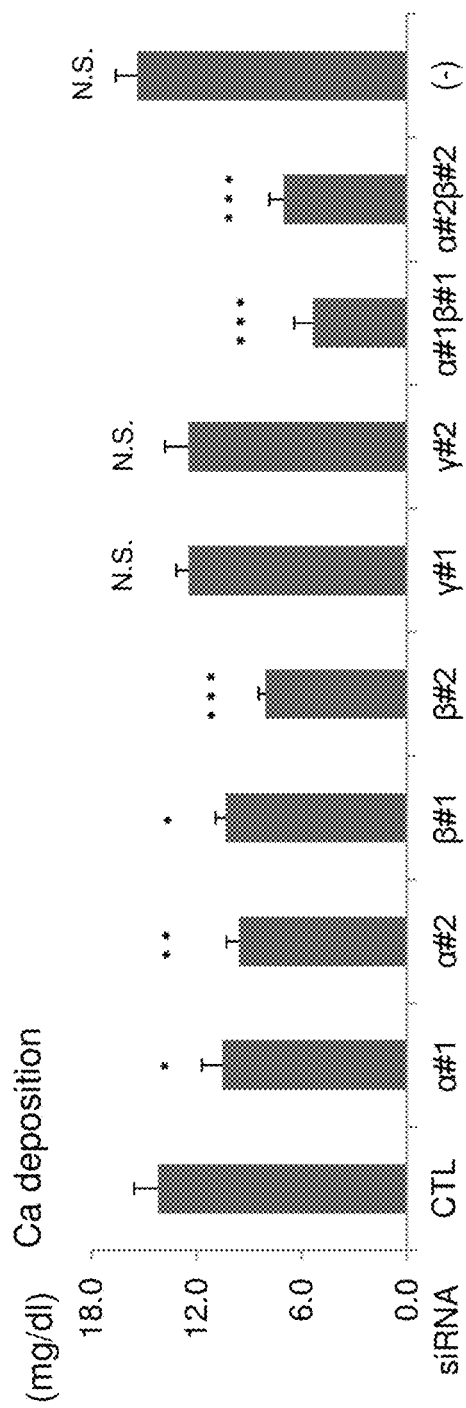
FIG. 13 shows the amount of calcium salt deposition when cells were induced to differentiate in culture medium supplemented with siRNAs against each retinoic acid receptor by the one-procedure osteogenic differentiation method of the present invention, as compared with the amount of calcium salt deposition when cells were induced to differentiate in the absence of siRNAs against retinoic acid receptors.

Next, the effects of siRNAs on each RAR were analyzed. Addition of siRNAs against RARγ (γ#1 and γ#2) showed no effects on the bone-forming capacity. However, addition of siRNAs against RARα (α#1 and α#2) and siRNAs against RARβ (β#1 and β#2) reduced the bone-forming capacity. Addition of siRNAs against RARα in combination with siRNAs against RARβ (α#1β#1 and α#2β#2) further reduced the bone-forming capacity (FIG. 13). In the figure, CTL indicates cell culture supplemented with a control siRNA, and (−) indicates cell culture with no siRNA.

(2) Induction of Differentiation Using Agonists Specific for Each Receptor

Figure 14:
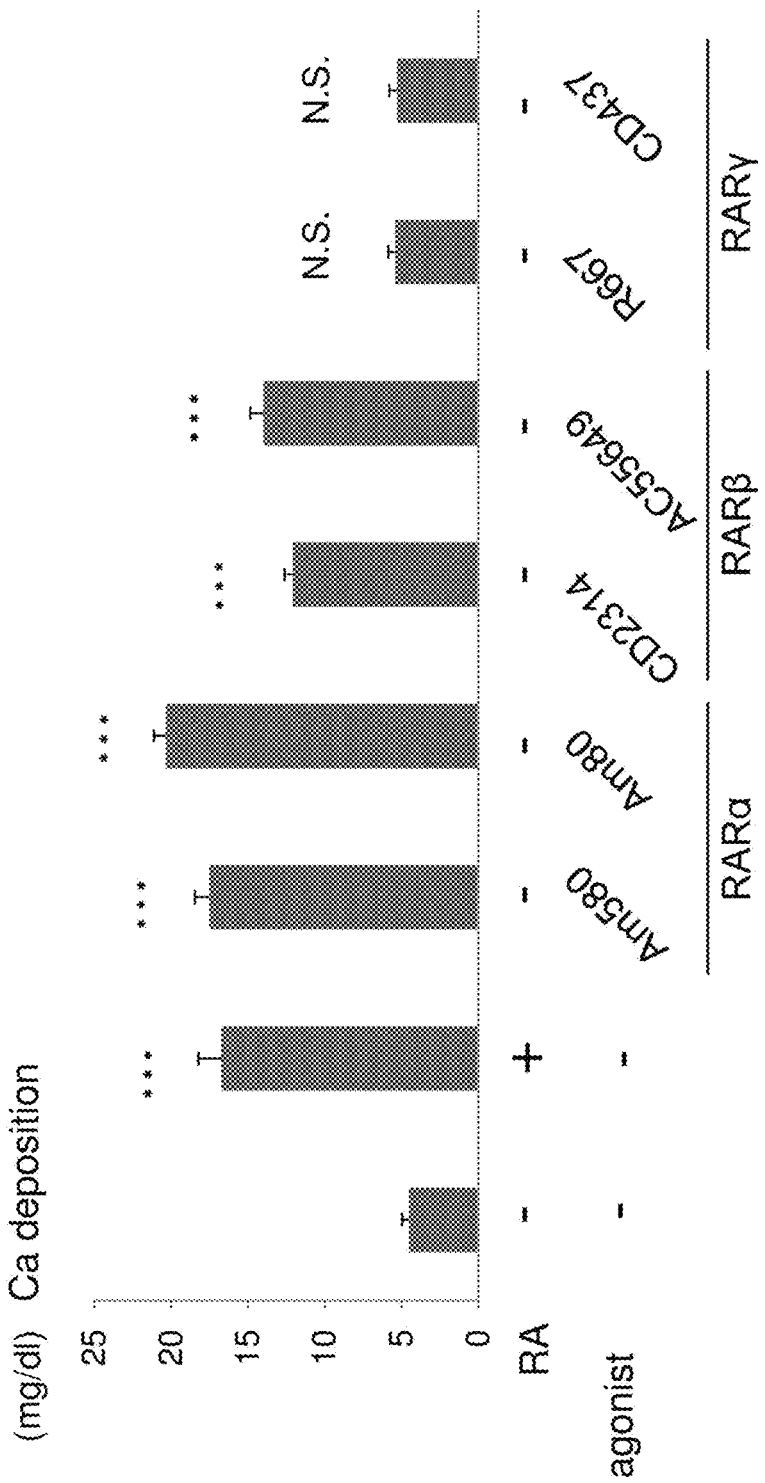
FIG. 14 shows the amount of calcium salt deposition when cells were induced to differentiate in culture medium supplemented with each of the indicated retinoic acid receptor agonists, instead of retinoic acid, by the one-procedure osteogenic differentiation method of the present invention.

Cells were subjected to the one-procedure osteogenic differentiation method in osteogenic induction medium supplemented with a retinoic acid receptor (RAR) agonist instead of retinoic acid (RA). The amount of calcium salt deposition was determined on day 10. The results are shown in FIG. 14. As with addition of retinoic acid, the amount of calcium salt deposition was increased by the addition of the RARα agonists Am 580 (200 nM) and Am 80 (1 μM), or the RARβ agonists CD2314 (3 μM) and AC 55649 (3 μM). However, such effects were not observed for the RARγ agonists R667 (100 nM) and CD437 (1 μM). The results indicate that the osteogenic differentiation-inducing activity of retinoic acid can be substituted with a RARα agonist or a RARβ agonist.

Example 4

Investigation of Recapitulation of Pathological Conditions of Bone Diseases

The inventors investigated whether the established one-procedure osteogenic differentiation method is useful for recapitulation of the pathological conditions of bone diseases. For this purpose, osteogenesis imperfecta (OI), a common skeletal dysplasia, was used as a model.

OI is a disease caused by abnormalities of type I collagen and characterized by increased bone tissue fragility, and can lead to frequent bone fractures. The molecular pathology of OI mainly includes collagen gene abnormalities and ER stress. Collagen gene abnormalities cause lack of formation of a normal collagen triple helix and result in reduction of collagen secretion, leading to abnormalities of the bone-forming capacity, such as reduction of mineralization. ER stress is induced by the accumulation of abnormal collagen in the endoplasmic reticulum (ER) and can lead to cell death.

(1) Recapitulation of Pathological Conditions Using iPS Cells Derived From OI Patients iPS cells (OI#1-1 and OI#2-1) were established from two OI patients (OI#1 and OI#2) having an abnormal COL1A1 gene. The respective mutations in the COL1A1 gene in the iPS cells were restored by genome editing technology to generate rescued iPS cells (resOI#1-1 and resOI#2-1). These iPS cells and standard iPS cells (WT1, 414C2; WT2, 409B2) were subjected to induction of osteogenic differentiation by the one-procedure osteogenic differentiation method. On day 10 of induction, the cells were compared in terms of the capacity of calcified nodule formation, the amount of calcium salt deposition, the expression of an ER stress-related gene, and the capacity of type I collagen secretion.

Figure 15:
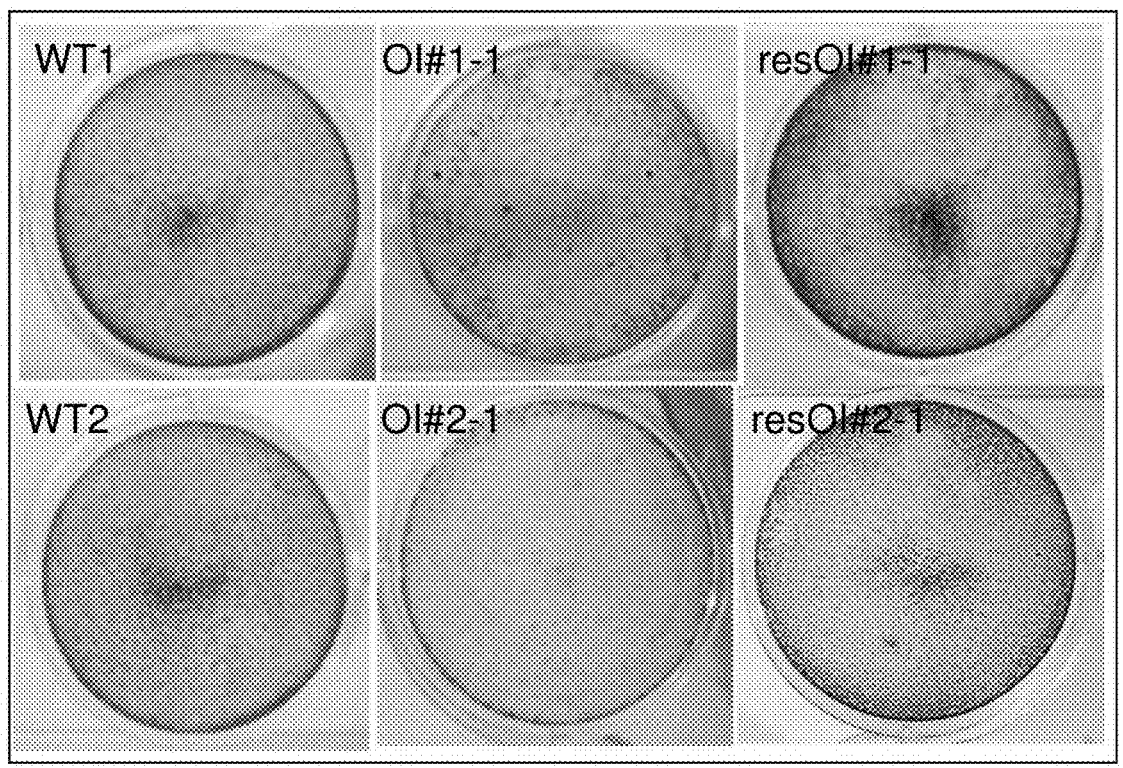
FIG. 15 shows the bone matrix-forming capacity of cells induced to differentiate from iPS cells, as assessed by alizarin red staining over time. iPS cells were derived from osteogenesis imperfecta patients having abnormalities of the COL1A1 gene. The respective mutations in the COL1A1 gene in the iPS cells were restored by genome editing technology to generate rescued iPS cells. The patient-derived iPS cells, the rescued iPS cells and standard iPS cells were subjected to induction of differentiation by the one-procedure osteogenic differentiation method of the present invention, and the induced cells were stained by alizarin red staining over time.
Figure 16:
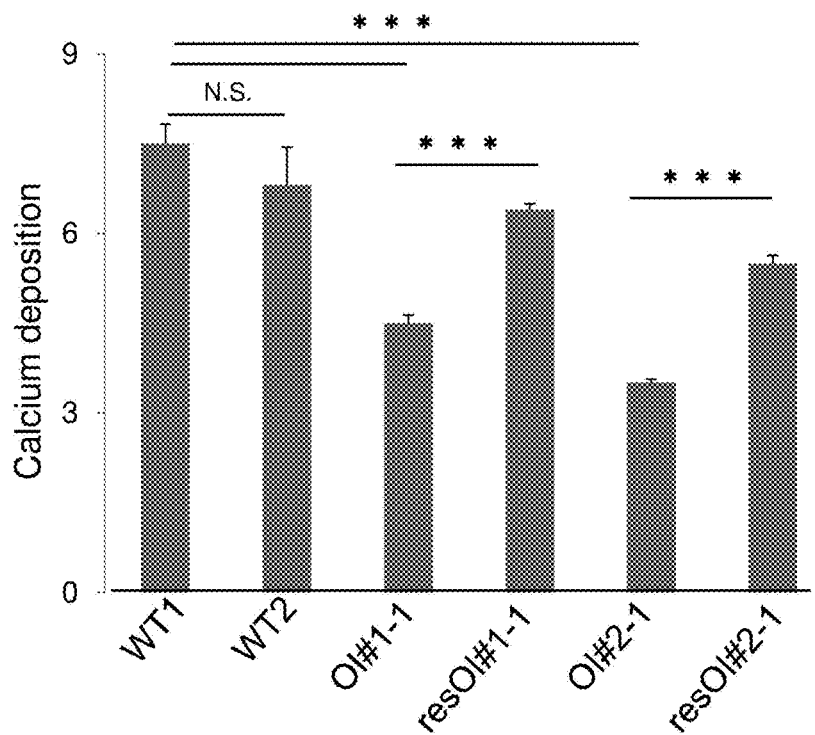
FIG. 16 shows the bone matrix-forming capacity of cells induced to differentiate from iPS cells, as assessed by the amount of calcium salt deposition measured over time. iPS cells were derived from osteogenesis imperfecta patients having abnormalities of the COL1A1 gene. The respective mutations in the COL1A1 gene in the iPS cells were restored by genome editing technology to generate rescued iPS cells. The patient-derived iPS cells, the rescued iPS cells and standard iPS cells were subjected to induction of differentiation by the one-procedure osteogenic differentiation method of the present invention, and the amount of calcium salt deposition was determined over time.
Figure 17:
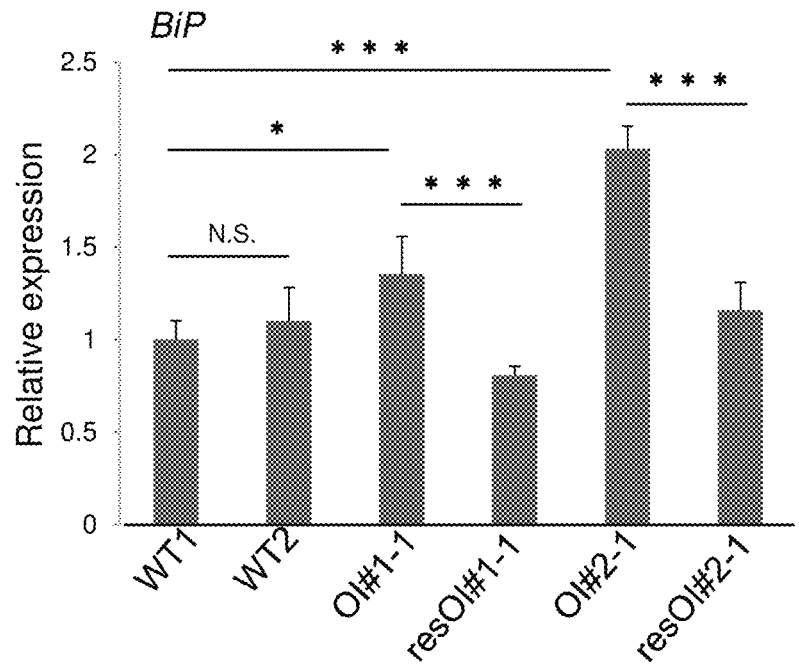
FIG. 17 shows the expression of an endoplasmic reticulum stress-related gene (BiP gene) in cells on days 7 and 10 of induction of differentiation from iPS cells. iPS cells were derived from osteogenesis imperfecta patients having abnormalities of the COL1A1 gene. The respective mutations in the COL1A1 gene in the iPS cells were restored by genome editing technology to generate rescued iPS cells. The patient-derived iPS cells, the rescued iPS cells and standard iPS cells were subjected to induction of differentiation by the one-procedure osteogenic differentiation method of the present invention, and the expression of the endoplasmic reticulum stress-related gene BiP in the induced cells was analyzed on days 7 and 10.

FIG. 15 shows alizarin red staining. FIG. 16 shows the amount of calcium salt deposition. FIG. 17 shows the expression of an ER stress-related gene. FIG. 18 shows the capacity of type I collagen secretion. OI#1-1 and OI#2-1 subjected to the one-procedure osteogenic differentiation method produced a smaller number of alizarin red-positive calcified nodules as compared with WT1 and WT2, whereas the number of alizarin red-positive calcified nodules was restored in the mutation rescued cells (resOI#1-1 and resOI#2-1) (FIG. 15). This tendency was more significant in the quantification of the amount of calcium salt deposition (FIG. 16). The expression of the ER stress-related gene BiP was elevated in OI#1-1 and OI#2-1, but decreased in resOI#1-1 and resOI#2-1 to the level of WT1 and WT2 (FIG. 17). Type I collagen secretion as assessed by immunostaining with anti-type I collagen antibody was decreased in OI#1-1 and OI#2-1 and its distribution was very uneven, but collagen secretion and distribution in resOI#1-1 and resOI#2-1 were the same levels as those of WT1 and WT2 (FIG. 18). The results indicate that the phenotypic changes observed in OI#1-1 and OI#2-1 are attributed to the respective mutations in the COL1A1 gene, demonstrating that the pathological conditions of the hereditary disease OI can be recapitulated in vitro by using the one-procedure osteogenic differentiation method together with iPS cells from disease patients.

Example 5

Application of the Method as a Screening Tool for Drug Discovery

Inhibition of mTOR protein complex by rapamycin has been reported to serve as a therapeutic strategy for OI, and demonstrated to enhance autophagy, thereby reducing the intracellular accumulation of unfolded proteins in primary cultured cells from patients. Accordingly, the inventors investigated whether the one-procedure osteogenic differentiation method can recapitulate the effects of an mTOR inhibitor. Rapamycin (10 nM) or everolimus (100 nM) was added to the culture medium from day 2 of the induction, and differentiation capacity was assessed on day 10.

FIG. 19 shows alizarin red staining. FIG. 20 shows the amount of calcium salt deposition. FIG. 21 shows the expression of the ER stress-related gene BiP. FIG. 22 shows type I collagen secretion capacity. The results demonstrate that addition of rapamycin or everolimus to the culture medium improves the capacity of forming alizarin red-positive calcified nodules and also improves the amount of calcium salt deposition. The results also suggested reduction of ER stress. Type I collagen secretion and distribution were also remarkably improved by addition of rapamycin or everolimus.

FIGS. 23A and 23B show the quantification of the amount of the accumulated intracellular type I collagen. FIG. 23A shows images of intracellular type I collagen immunostained with anti-type I collagen antibody. FIG. 23B shows the amount of accumulated intracellular type I collagen quantitatively determined from the images of FIG. 23A by an image analysis software. FIG. 23A demonstrates that type I collagen is primarily localized within the cells when induced to differentiate in the absence rapamycin (Vehicle) and weak staining is observed in the extracellular matrix, whereas intracellular staining is weak in the cells when induced to differentiate in culture medium supplemented with rapamycin. FIG. 23B reveals that reduction of the amount of accumulated intracellular type I collagen by addition of rapamycin is statistically significant.

The results indicate that the one-procedure osteogenic differentiation method can be used to assess the efficacy of a candidate therapeutic drug.

The present invention is not limited to each of the embodiments and Examples as described above, and various modifications are possible within the scope of the claims. Embodiments obtainable by appropriately combining the technical means disclosed in the different embodiments of the present invention are also included in the technical scope of the present invention. The contents of the scientific literature and the patent literature cited herein are hereby incorporated by reference in their entirety.

The invention claimed is:

1. A method for inducing osteogenic differentiation, the method comprising the following steps of:
   (1) culturing pluripotent stem cells under feeder-free conditions,
   (2) culturing the cells in a mixed culture medium of an osteogenic induction medium and a pluripotent stem cell medium, the mixed culture medium containing a ROCK inhibitor and a retinoic acid receptor α or β agonist, and
   (3) culturing the cells in an osteogenic induction medium containing the retinoic acid receptor α or β agonist,
   wherein the method does not comprise a step of forming embryoid bodies.

2. The method for inducing osteogenic differentiation according to claim 1, wherein the total duration of the culturing steps (2) and (3) is 12 days or less.

3. The method for inducing osteogenic differentiation according to claim 1, wherein the duration of the culturing step (2) is 2 days.

4. A method for screening for a therapeutic drug for a bone disease, the method comprising the following steps of:
   (I) culturing pluripotent stem cells under feeder-free conditions,
   (II) culturing the cells in a mixed culture medium of an osteogenic induction medium and a pluripotent stem cell medium, the mixed culture medium containing a ROCK inhibitor and a retinoic acid receptor α or β agonist,
   (III) culturing the cells in an osteogenic induction medium containing the retinoic acid receptor α or β agonist and a test substance,
   (IV) measuring at least one selected from the amount of calcified nodule formation, the amount of calcium salt deposition, the production or secretion level of type I collagen, and the expression level of an osteogenic differentiation-related gene, and
   (V) comparing a measured value with that of the cells cultured in an osteogenic induction medium free of the test substance to determine whether the test substance is capable of enhancing osteogenic differentiation capacity of the cells,
   wherein the method does not comprise a step of forming embryoid bodies.

5. The screening method according to claim 4, wherein the total duration of the culturing steps (II) and (III) is 12 days or less.

6. The screening method according to claim 4, wherein the duration of the culturing step (II) is 2 days.

7. The screening method according to claim 4, wherein the pluripotent stem cells are bone disease-model pluripotent stem cells.

8. The screening method according to claim 7, wherein the bone disease-model pluripotent stem cells are iPS cells prepared from cells of a patient with a bone disease.

9. The screening method according to claim 4, wherein the pluripotent stem cells are healthy human-derived pluripotent stem cells free of abnormalities associated with a bone disease.

* * * * *